United States Patent [19]
Bluestone et al.

[11] Patent Number: 5,885,573
[45] Date of Patent: Mar. 23, 1999

[54] METHODS AND MATERIALS FOR MODULATION OF THE IMMUNOSUPPRESSIVE ACTIVITY AND TOXICITY OF MONOCLONAL ANTIBODIES

[75] Inventors: Jeffrey A. Bluestone, Chicago, Ill.; Robert A. Zivin, Lawrenceville; Linda K. Jolliffe, Somerville, both of N.J.

[73] Assignees: Arch Development Corporation, Chicago, Ill.; Ortho Pharmaceutical Corporation, Raritan, N.J.

[21] Appl. No.: 70,116

[22] Filed: Jun. 1, 1993

[51] Int. Cl.[6] .................................................. A61K 39/395
[52] U.S. Cl. .................................... 424/133.1; 424/144.1; 530/387.3; 530/388.22; 435/240.27
[58] Field of Search ............................ 530/387.3, 388.75; 435/240.2, 240.27; 424/133.1, 136.1, 154.1

[56] References Cited

U.S. PATENT DOCUMENTS

| | | | |
|---|---|---|---|
| 4,658,019 | 4/1987 | Kung et al. | 530/388.75 |
| 4,695,624 | 9/1987 | Marburg et al. | . |
| 4,830,852 | 5/1989 | Marburg et al. | . |
| 4,882,317 | 11/1989 | Marburg et al. | . |
| 5,624,821 | 4/1997 | Winter et al. | . |

FOREIGN PATENT DOCUMENTS

WO 91/09968  7/1991  WIPO .

OTHER PUBLICATIONS

Alegre et al., "A Non–Activating Humanized Anti–CD3 Monoclonal Antibody Retains Immunosuppresive Properties In Vivo," *Transplantation*, 57(11):1537–1543, 1994.

Alegre et al., "Effect of a Single Amino Acid Mutation on the Activating and Immunosuppresive Properties of a Humanized OKT3 Monoclonal Antibody," *The Journal of Immunology*, 148(11):3461–3468, 1992.

Ortho Multicenter Transplant Study Group, "A Randomized Clinical Trial of OKT3 Monoclonal Antibody for Acute Rejection of Gadaveric Renal Transplants," *The New England Journal of Medicine*, 313(6):337–342, 1985.

Thistlehwaite, Jr. et al., "OKT3 Treatment of Steroid–Resistant Renal Allograft Rejection," *Transplantation*, 43(2):176–184, 1997.

Chatenoud et al., "Systematic Reaction to the Anti–T–Cell Monoclonal Antibody OKT3 in Relation to Serum Levels of Tumor Necrosis Factor and Interferon–$\alpha$," *The New England Journal of Medicine*, 320(41):1420–1421.

Parlevliet et al., "Anti–CD3 Murine Monoclonal Isotype Switch Variants Tested for Toxicity and Immunologic Monitoring in Four Chimpanzees," *Transplantation*, 50(5):889–892, 1990.

Alegre et al., "Cytokine Release Syndrome Induced by the 145–2C11 Anti–CD3 Monoclonal Antibody in Mice: Prevention by High Doses of Methylprednisolone," *The Journal of Immunology*, 146(4):1184–1191, 1991.

Waid et al., "Treatment of Acute Cellular Rejection with T10B9.1A–31 or OKT3 in Renal Allograft Recipients," *Transplantation*, 53(1):80–86, 1992.

Woodle et al., "Humanized OKT3 Antibodies: Successful Transfer of Immune Modulating Properties and Idiotype Expression," *The Journal of Immunology*, 148(9):2756–2763, 1992.

Burton, "Immunoglobin G: Functional Sites," *Monocular Immunology*, 22(3):161–206, 1985.

Partridge et al., "The Use of Anti–IgG Monoclonal Antibodies in Mapping the Monocyte Receptor Site in IgG," *Molecular Immunology*, 23(12):1365–1372, 1986.

Duncan et al., "Localization of the binding site for the human high–affinity Fc receptor on IgG," *Nature*, 332:563–564, 1988.

Jefferis et al., "Molecular Definition of Interaction Sites on Human IgG for Fc Receptors (huFc$\gamma$R)," *Molecular Immunology*, 27(12):1237–1240, 1990.

Gergely and Sarmay, "The two binding–site models of human IgG binding Fc$\gamma$ receptors," *The FASEB Journal*, 4:3275–3283, 1990.

Bolt et al., "The Generation of a Humanized, Non–mitogenic CD3 Monoclonal Antibody Which Retains in vitro Immunosuppressive Porperties," *Eur. J. Immunol.*, 23:403–411, 1993.

Jolliffe, Linda K., "Humanized Antibodies; Enhancing Therapeutic Utility Through Antibody Engineering," *Intern. Rev. Immunol.*, 10:241–250, 1993.

Alegre et al. J. Am. Soc. Nephrol. 2(3), 530, 1991.

Harlow et al., Antibodies a Laboratory Manual, Cold Spring Harbor Laboratory Press 1988, pp. 285, 287.

*Primary Examiner*—Paula K. Hutzell
*Attorney, Agent, or Firm*—Arnold, White & Durkee

[57] ABSTRACT

The binding specificity of the murine OKT3 has been transferred into a human antibody framework in order to reduce its immunogenicity. This "humanized" anti-CD3 mAb (gOKT3-5) was previously shown to retain, in vitro, all the properties of native OKT3, including T cell activation which has been correlated, in vivo, with the severe side-effects observed in transplant recipients after the first administration of the mAb. Disclosed is a single amino acid mutation from a leucine to a glutamic acid at position 235 in the Fc receptor (FcR) binding segment of the gOKT3-5 mAb to produce Glu-235 mAb. Also disclosed is an amino acid mutation from the contiguous phenylalanine at position 234 to a leucine (Leu-234).

3 Claims, 27 Drawing Sheets

LIGHT CHAIN

```
                10         20         30         40         50
Okt3vl  QIVLTQSPAIMSASPGEKVTMTCSASS-SVSYMNWYQQKSGTSPKRWIYDTSKLAS    SEQ ID NO:6
REI     DIQMTQSPSSLSASVGDRVTITCQASQDIIKYLNWYQQTPGKAPKLLIYEASNLQA    SEQ ID NO:7
gL      ..........................SA.S-SVS.M...........DT.K.AS     SEQ ID NO:8
gLC     ..........................SA.S-SVS.M........RW..DT.K.AS    SEQ ID NO:9

60         70         80         90        100  108
OKT3VL  GVPAHFRGSGSGTSYSLTISGMEAEDAATYYCQQWSSNPFTFGSGTKLEINR         SEQ ID NO:6
REI     GVPSRFSGSGSGTDYTFTISSLQPEDIATYYCQQYQSLPYTFGQGTKLQITR         SEQ ID NO:7
gL      ...........................WS.N.F..........                SEQ ID NO:8
gLC     ...........................WS.N.F..........                SEQ ID NO:9
```

FIG. 1A

HEAVY CHAIN

```
              10         20         30
Okt3vh   QVQLQQSGAELARPGASVKMSCKASGYTFTRY    SEQ ID NO:10
KOL      QVQLVESGGGVVQPGRSLRLSCSSSGFIFSSY    SEQ ID NO:11
gH       .........................YT.TR.    SEQ ID NO:12
gHA      .....Q...............KA..YT.TR.    SEQ ID NO:13
gHG      .....Q...............KA..YT.TR.    SEQ ID NO:14

40         50         60
Okt3vh   TMHWVKQRPGQGLEWIGYINPSRGYTNYNQKF    SEQ ID NO:10
KOL      AMYWVRQAPGKGLEWVAIIWDDGSDQHYADSV    SEQ ID NO:11
gH       T.H............Y.NPSRGYTN.NQKF     SEQ ID NO:12
gHA      T.H...........IGY.NPSRGYTN.NQK.    SEQ ID NO:13
gHG      T.H...........IGY.NPSRGTYN.NQK.    SEQ ID NO:14

70         80         90
Okt3vh   KDKATLTTDKSSSTAYMQLSSLTSEDSAVYYC    SEQ ID NO:10
KOL      KGRFTISRDNSKNTLFLQMDSLRPEDTGVYFC    SEQ ID NO:11
gH       .D.............................    SEQ ID NO:12
gHA      .D.....T.K..S.A............A..Y.   SEQ ID NO:13
gHG      .D............A.................   SEQ ID NO:14

100        110       120   126
Okt3vh   ARYYDDHYCL------DYWGQGTTLTVSS      SEQ ID NO:10
KOL      ARDGGHGFCSSASCFGPDYWGQGTPVTVSS     SEQ ID NO:11
gH       ..YYDDHY.L------...............    SEQ ID NO:12
gHA      ..YYDDHY.L------...............    SEQ ID NO:13
gHG      ..YYDDHY.L------...............    SEQ ID NO:14
```

FIG. 1B

```
                    5        10       15       20       25       30       35       40       45       50       55
                    *        *        *        *        *        *        *        *        *        *        *
          ATCCTGGCAA AGATTGTAAT ACGACTCACT ATAGGGCGAA TTCGCCGCCA CC ATG GAA
                                                                  Met Glu>
                                                                  ___a____>

60       65       70       75       80       85       90       95       100      105
           *        *        *        *        *        *        *        *        *        *
          TGG AGC TGG GTC TTT CTC TTC CTG TCA GTA ACT ACA GGT GTC CAC
          Trp Ser Trp Val Phe Leu Phe Leu Ser Val Thr Thr Gly Val His>
          __a____TRANSLATION OF OKT3 HC IGG4 12/4/92 [A]_a____a____a___>

110      115      120      125      130      135      140      145      150
           *        *        *        *        *        *        *        *        *
          TCC CAG GTT CAG CTG GTG CAG TCT GGA GGA GGA GTC GTC CAG CCT GGA
          Ser Gln Val Gln Leu Val Gln Ser Gly Gly Gly Val Val Gln Pro Gly>
          __a____TRANSLATION OF OKT3 HC IGG4 12/4/92 [A]_a____a____a___>

155 160      165      170      175      180      185      190      195      200
                *        *        *        *        *        *        *        *        *
          AGG TCC CTG AGA CTG TCT TGT AAG GCT TCT GGA TAC ACC TTC ACT AGA
          Arg Ser Leu Arg Leu Ser Cys Lys Ala Ser Gly Tyr Thr Phe Thr Arg>
          __a____TRANSLATION OF OKT3 HC IGG4 12/4/92 [A]_a____a____a___>
```

FIG. 2A

```
       205       210       215       220       225       230       235       240       245       250
        *         *         *         *         *         *         *         *         *         *
       TAC ACA ATG CAC TGG GTC AGA CAG GCT CCT GGA AAG GGA CTC GAG TGG
       Tyr Thr Met His Trp Val Arg Gln Ala Pro Gly Lys Gly Leu Glu Trp>
       a_____a_____a    TRANSLATION OF OKT3 HC IGG4 12/4/92 [A]_a_____a_____a_____>

255       260       265       270       275       280       285       290       295
        *         *         *         *         *         *         *         *         *
       ATT GGA TAC ATT AAT CCT AGC AGA GGT TAT ACT AAC TAC AAT CAG AAG
       Ile Gly Tyr Ile Asn Pro Ser Arg Gly Tyr Thr Asn Tyr Asn Gln Lys>
       a_____a_____a    TRANSLATION OF OKT3 HC IGG4 12/4/92 [A]_a_____a_____a_____>

300       305       310       315       320       325       330       335       340       345
        *         *         *         *         *         *         *         *         *         *
       GTG AAG GAC AGA TTC ACA ATT TCT AGA GAC AAT TCT AAG AAT ACA GCC
       Val Lys Asp Arg Phe Thr Ile Ser Arg Asp Asn Ser Lys Asn Thr Ala>
       a_____a_____a    TRANSLATION OF OKT3 HC IGG4 12/4/92 [A]_a_____a_____a_____>

350       355       360       365       370       375       380       385       390
        *         *         *         *         *         *         *         *         *
       TTC CTG CAG ATG GAC TCA CTC AGA CCT GAG GAT ACC GGA GTC TAT TTT
       Phe Leu Gln Met Asp Ser Leu Arg Pro Glu Asp Thr Gly Val Tyr Phe>
       a_____a_____a    TRANSLATION OF OKT3 HC IGG4 12/4/92 [A]_a_____a_____a_____>
```

FIG. 2B

```
395   400        405        410        415        420        425        430        435        440
  *                *          *          *          *          *          *          *          *
TGT GCT AGA TAT TAC GAT GAC CAC TGT CTG GAC TAC TGG GGC CAA
Cys Ala Arg Tyr Tyr Asp Asp His Tyr Cys Leu Asp Tyr Trp Gly Gln>
    a     a    TRANSLATION OF OKT3 HC IGG4 12/4/92 [A]_a____a____a____a____>

>SEQED_(include)_of:_ja91.ins_check:_5694_from:_1_to:_2153

445   450        455        460        465        470        475        480        485        490
  *                *          *          *         |*          *          *          *          *
GGT ACC CCG GTC ACC GTG AGC TCA GCT TCC ACC AAG GGC CCA TCC GTC
Gly Thr Pro Val Thr Val Ser Ser Ala Ser Thr Lys Gly Pro Ser Val>
    a     a    TRANSLATION OF OKT3 HC IGG4 12/4/92 [A]_a____a____a____a____>

495   500        505        510        515        520        525        530        535
  *                *          *          *          *          *          *          *
TTC CCC CTG GCG CCC TGC TCC AGG AGC ACC TCC GAG AGC ACA GCC GCC
Phe Pro Leu Ala Pro Cys Ser Arg Ser Thr Ser Glu Ser Thr Ala Ala>
    a     a    TRANSLATION OF OKT3 HC IGG4 12/4/92 [A]_a____a____a____a____>
```

FIG. 2C

```
540   545   550   555   560   565   570   575   580   585
 *           *           *           *           *
CTG GGC TGC CTG GTC AAG GAC TAC TTC CCC GAA CCG GTG ACG GTG TCG
Leu Gly Cys Leu Val Lys Asp Tyr Phe Pro Glu Pro Val Thr Val Ser>
 a   a       TRANSLATION OF OKT3 HC IGG4 12/4/92  [A] a   a   a 590   595   600   605   610   615   620   625   630
 *           *           *           *
TGG AAC TCA GGC GCC CTG ACC AGC GGC GTG CAC ACC TTC CCG GCT GTC
Trp Asn Ser Gly Ala Leu Thr Ser Gly Val His Thr Phe Pro Ala Val>
 a   a       TRANSLATION OF OKT3 HC IGG4 12/4/92  [A] a   a   a 635 640   645   650   655   660   665   670   675   680
     *           *           *           *           *
CTA CAG TCC TCA GGA CTC TAC TCC CTC AGC AGC GTG GTG ACC GTG CCC
Leu Gln Ser Ser Gly Leu Tyr Ser Leu Ser Ser Val Val Thr Val Pro>
 a   a       TRANSLATION OF OKT3 HC IGG4 12/4/92  [A] a   a   a 685   690   695   700   705   710   715   720   725   730
 *           *           *           *           *
TCC AGC AGC TTG GGC ACG AAG ACC TAC ACC TGC AAC GTA GAT CAC AAG
Ser Ser Ser Leu Gly Thr Lys Thr Tyr Thr Cys Asn Val Asp His Lys>
 a   a       TRANSLATION OF OKT3 HC IGG4 12/4/92  [A] a   a   a
```

FIG. 2D

```
     735     740     745     750     755     760     765     770     775     780
      *       *       *       *       *       *       *       *       *       *
CCC AGC AAC ACC AAG GTG GAC AAG AGA GTT GGTGAGAGGC CAGCACAGGG
Pro Ser Asn Thr Lys Val Asp Lys Arg Val>
    TRANSLATION OF OKT3 HC IGG4 12/4          >

785     790     795     800     805     810     815     820     825     830     835     840
  *       *       *       *       *       *       *       *       *       *       *       *
AGGGAGGGTG TCTGCTGGAA GCCAGGCTCA GCCCTCCTGC CTGGACGCAC CCCGGCTGTG
     845     850     855     860     865     870     875     880     885     890     895     900
      *       *       *       *       *       *       *       *       *       *       *       *
CAGCCCCCAGC CCAGGGCAGC AAGGCATGCC CCATCTGTCT CCTCACCCGG AGGCCTCTGA
 905     910     915     920     925     930     935     940     945     950     955     960
  *       *       *       *       *       *       *       *       *       *       *       *
CCACCCCACT CATGCTCAGG GAGAGGGTCT TCTGGATTTT TCCACCAGGC TCCCGGCACC
 965     970     975     980     985     990     995    1000    1005    1010    1015    1020
  *       *       *       *       *       *       *       *       *       *       *       *
ACAGGCTGGA TGCCCCTACC CCAGGCCCTG CGCATACAGG GCAGGTGCTG CGCTCAGACC
```

FIG. 2E

```
          1025 1030 1035 1040 1045 1050 1055 1060 1065 1070 1075 1080
             *         *         *         *         *         *
      TGCCAAGAGC CATATCCGGG AGGACCCTGC CCCTGACCTA AGCCCACCCC AAAGGCCAAA 1085 1090 1095 1100 1105 1110 1115 1120 1125 1130 1135 1140
             *         *         *         *         *         *
      CTCTCCACTC CCTCAGCTCA GACACCTTCT CTCCTCCCAG ATCTGAGTAA CTCCCAATCT 1145 1150 1155 1160 1165 1170 1175 1180 1185 1190
             *         *         *         *         *
      TCTCTCTGCA GAG TCC AAA TAT GGT CCC CCA TGC CCA TCA TGC CCA GGTA
              Glu Ser Lys Tyr Gly Pro Pro Cys Pro Ser Cys Pro>
              TRANSLATION OF OKT3 HC IGG4 12/4/92 [A]_b___>

1195 1200 1205 1210 1215 1220 1225 1230 1235 1240 1245 1250
             *         *         *         *         *         *
      AGCCAACCCA GGCCTCGCCC TCCAGCTCAA GGCGGGACAG GTGCCCTAGA GTAGCCTGCA 1255 1260 1265 1270 1275 1280 1285 1290 1295 1300 1305 1310
             *         *         *         *         *         *
      TCCAGGGACA GGCCCCAGCC GGGTGCTGAC GCATCCACCT CCATCTCTTC CTCAGCA CCT
                                                                   Pro>
                                                                   ___^
```

FIG. 2F

```
     1315      1320 1325      1330      1335      1340      1345      1350 1355
                *                                   *                          *
GAG TTC CTG GGG GGA CCA TCA GTC TTC CTG TTC CCC CCA AAA CCC AAG
Glu Phe Leu Gly Gly Pro Ser Val Phe Leu Phe Pro Pro Lys Pro Lys>
  c                c   TRANSLATION OF OKT3 HC IGG4 12/4/92 [A] c   c   c    >

1360 1365      1370      1375      1380 1385      1390      1395 1400      1405
  *              *                   *                   *
GAC ACT CTC ATG ATC TCC CGG ACC CCT GAG GTC ACG TGC GTG GTG GTG
Asp Thr Leu Met Ile Ser Arg Thr Pro Glu Val Thr Cys Val Val Val>
   c        c      TRANSLATION OF OKT3 HC IGG4 12/4/92 [A] c   c   c    >

1410 1415      1420      1425      1430      1435      1440 1445      1450
  *                  *                   *                   *
GAC GTG AGC CAG GAA GAC CCC GAG GTC CAG TTC AAC TGG TAC GTG GAT
Asp Val Ser Gln Glu Asp Pro Glu Val Gln Phe Asn Trp Tyr Val Asp>
   c   c         TRANSLATION OF OKT3 HC IGG4 12/4/92 [A] c   c   c    >

1455 1460 1465      1470 1475      1480      1485 1490      1495 1500
                      *                        *                          *
GGC GTG GAG GTG CAT AAT GCC AAG ACA AAG CCG CGG GAG GAG CAG TTC
Gly Val Glu Val His Asn Ala Lys Thr Lys Pro Arg Glu Glu Gln Phe>
   c                   TRANSLATION OF OKT3 HC IGG4 12/4/92 [A] c   c   c    >
```

FIG. 2G

```
1505 1510 1515 1520 1525 1530 1535 1540 1545 1550
 *         *         *         *         *         *         *         *         *         *
AAC AGC ACG TAC CGT GTG GTC AGC GTC CTC ACC GTC CTG CAC CAG GAC
Asn Ser Thr Tyr Arg Val Val Ser Val Leu Thr Val Leu His Gln Asp>
       c     c       TRANSLATION OF OKT3 HC IGG4 12/4/92 [A] c    c       c        >

1555 1560 1565 1570 1575 1580 1585 1590 1595
 *         *         *         *         *         *         *         *         *
TGG CTG AAC GGC AAG GAG TAC AAG TGC AAG GTC TCC AAC AAA GGC CTC
Trp Leu Asn Gly Lys Glu Tyr Lys Cys Lys Val Ser Asn Lys Gly Leu>
  c     c       TRANSLATION OF OKT3 HC IGG4 12/4/92 [A] c       c         >

1600 1605 1610 1615 1620 1625 1630 1635 1640 1645 1650
 *         *         *         *         *         *         *         *         *         *
CCG TCC TCC ATC GAG AAA ACC ATC TCC AAA GCC AAA GGT GGG ACCCACGGGG
Pro Ser Ser Ile Glu Lys Thr Ile Ser Lys Ala Lys>
     TRANSLATION OF OKT3 HC IGG4 12/4/92 [A] c        >

1655 1660 1665 1670 1675 1680 1685 1690 1695 1700 1705 1710
 *         *         *         *         *         *         *         *         *         *         *         *
TGCGAGGGCC ACACGGACAG AGGCCAGCTC GGCCCACCCT CTGCCCTGGG AGTGACCGCT
```

FIG. 2H

```
1715 1720 1725 1730      1735 1740 1745      1750 1755 1760
  *              *              *              *         *
GTGCCAACCT CTGTCCCTAC A GGG CAG CCC CGA GAG CCA CAG GTG TAC ACC
                        Gly Gln Pro Arg Glu Pro Gln Val Tyr Thr>
                        ──── TRANSLATION OF OKT3 HC IGG4 12/4────

1765 1770 1775      1780 1785 1790      1795 1800 1805
  *              *              *              *
CTG CCC CCA TCC CAG GAG GAG ATG ACC AAG AAC CAG GTC AGC CTG ACC
Leu Pro Pro Ser Gln Glu Glu Met Thr Lys Asn Gln Val Ser Leu Thr>
___d____d_____ TRANSLATION OF OKT3 HC IGG4 12/4/92 [A]_d____d____d_____

1810 1815 1820      1825 1830 1835      1840 1845 1850 1855
  *              *              *              *         *
TGC CTG GTC AAA GGC TTC TAC CCC AGC GAC ATC GCC GTG GAG TGG GAG
Cys Leu Val Lys Gly Phe Tyr Pro Ser Asp Ile Ala Val Glu Trp Glu>
___d____d_____ TRANSLATION OF OKT3 HC IGG4 12/4/92 [A]_d____d____d_____

1860 1865 1870      1875 1880 1885      1890 1895 1900 1905
  *              *              *              *         *
AGC AAT GGG CAG CCG GAG AAC AAC TAC AAG ACC ACG CCT CCC GTG CTG
Ser Asn Gly Gln Pro Glu Asn Asn Tyr Lys Thr Thr Pro Pro Val Leu>
___d____d_____ TRANSLATION OF OKT3 HC IGG4 12/4/92 [A]_d____d____d_____
```

FIG. 2I

```
      1910      1915      1920      1925      1930      1935      1940      1945      1950
        *         *         *         *         *         *         *         *         *
GAC TCC GAC GGC TCC TTC CTC TAC AGC AGG CTA ACC GTG GAC AAG
Asp Ser Asp Gly Ser Phe Leu Tyr Ser Arg Leu Thr Val Asp Lys>
|__d___d_____TRANSLATION OF OKT3 HC IGG4 12/4/92 [A]_d____d____d____|

1955 1960      1965      1970      1975      1980      1985      1990      1995      2000
        *         *         *         *         *         *         *         *         *
AGC AGG TGG CAG GAG GGG AAT GTC TTC TCA TGC TCC GTG ATG CAT GAG
Ser Arg Trp Gln Glu Gly Asn Val Phe Ser Cys Ser Val Met His Glu>
|__d____d_____TRANSLATION OF OKT3 HC IGG4 12/4/92 [A]_d____d____d____|

2005 2010 2015      2020      2025      2030      2035      2040      2045
             *         *         *         *         *         *         *         *
GCT CTG CAC AAC CAC TAC ACA CAG AAG AGC CTC TCC CTG TCT CTG GGT
Ala Leu His Asn His Tyr Thr Gln Lys Ser Leu Ser Leu Ser Leu Gly>
|__d____d_____TRANSLATION OF OKT3 HC IGG4 12/4/92 [A]_d____d____d____|

2050 2055 2060 2065 2070      2075 2080 2085 2090      2095 2100
        *                        *                        *
AAA TGA GTGCC AGGGCCGGCA AGCCCCCGCT CCCCGGGCTC TCGGGGTCGC
Lys ***>
|___d___>
```

FIG. 2J

```
       2105 2110 2115 2120 2125 2130 2135 2140 2145 2150 2155 2160
          *         *         *         *         *         *
       GCGAGGATGC TTGGCACGTA CCCCGTCTAC ATACTTCCCA GGCACCCAGC ATGGAAATAA 2165 2170 2175 2180 2185 2190 2195 2200 2205 2210 2215 2220
          *         *         *         *         *         *
       AGCACCCACC ACTGCCCTGG GCCCCTGTGA GACTGTGATG GTTCTTTCCA CGGGTCAGGC 2225 2230 2235 2240 2245 2250 2255 2260 2265 2270 2275 2280
          *         *         *         *         *         *
       CGAGTCTGAG GCCTGAGTGA CATGAGGGAG GCAGAGCGGG TCCCACTGTC CCCACACTGG 2285 2290 2295 2300 2305 2310 2315 2320 2325 2330 2335 2340
          *         *         *         *         *         *
       CCCAGGGCGTT GCAGTGTGTC CTGGGCCACC TAGGGTGGGG CTCAGCCAGG GGCTCCCTCG 2345 2350 2355 2360 2365 2370 2375 2380 2385 2390 2395
          *         *         *         *         *
       GCAGGGTGGG GCATTTGCCA GCGTGGCCCT CCCTCCAGCA GCAGGACTCT AGAGGATCC
```

FIG. 2K

| Isotype | 234 | 235 | 236 | 237 | 238 | 239 |
|---|---|---|---|---|---|---|
| | | N-terminal of CH2 domain | | | | |
| hIgG4 | Phe | Leu | Gly | Gly | Pro | Ser |

FIG. 6

METHODS AND MATERIALS FOR MODULATION OF THE IMMUNOSUPPRESSIVE ACTIVITY AND TOXICITY OF MONOCLONAL ANTIBODIES

FIELD OF THE INVENTION

This invention relates generally to methods and materials for modulation of the immunological activity and toxicity of immunosuppressive agents derived from murine OKT3 used in organ transplantation and in the treatment of auto-immune diseases.

BACKGROUND OF THE INVENTION

OKT3 is a murine monoclonal antibody (mAb) which recognizes an epitope on the ε-subunit within the human CD3 complex (Salmeron, 1991; Transy, 1989; see also, U.S. Pat. No. 4,658,019, herein incorporated by reference). In vitro studies have demonstrated that OKT3 possesses potent T-cell activating and suppressive properties depending on the assay used (Landgren, 1982; Van Seventer, 1987; Weiss, 1986). Binding of OKT3 to the T-cell receptor (TcR) results in coating of the TcR and or modulation, thus mediating TcR blockade, and inhibiting alloantigen recognition and cell-mediated cytotoxicity. Fc receptor-mediated cross-linking of TcR-bound anti-CD3 mAb results in T-cell activation marker expression, and proliferation (Weiss, 1986). Similarly, in vivo administration of OKT3 results in both T-cell activation and suppression of immune responses (Ellenhorn, 1992; Chatenoud, 1990). Repeated daily administration of OKT3 results in profound immunosuppression, and provides effective treatment of rejection following renal transplantation (Thistlethwaite, 1984).

The production of an immune response to rodent mAbs is a major obstacle to their therapeutic use. Several groups have reported attempts to circumvent this problem by reconstructing the rodent antibody genes by replacing immunogenic murine constant region sequences by the equivalent human antibody sequences (reviewed in Adair, 1992). In cases such as these, there is still the potential to mount an immune response against the variable region. In a further extension of the procedure, the variable region framework regions have been replaced with equivalent sequences from human variable region genes. From an examination of available X-ray structures of antigen-antibody complexes (reviewed in Poljak, 1991) it is probable that only a small number of antibody residues make direct contact with antigen. Other amino acids may contribute to antigen binding by positioning the contact residues in favorable configurations and also by inducing a stable packing of the individual variable domains, and stable interaction of the light and heavy chain variable domains. The antibody domains have been the subject of detailed examination and much has been published about the organization of the variable regions (see for example, Looney, 1986, and references therein) which can be applied to the design of the humanized antibody.

The use of OKT3 is limited by problems of "first dose" side effects, ranging from mild flu-like symptoms to severe toxicity, which are believed to be caused by lymphokine production stimulated by OKT3. Although successful reuse of OKT3 has been reported (Woodle, 1991) it is complicated by a human anti-mouse antibody (HAMA) response (Ortho Health Center Transplant Study Group, 1985), a proportion of the response being directed to the variable region of the antibody (Jaffers, 1984). While low titre HAMA may present no significant problem, some patients do develop high titre anti-isotype and/or anti-idiotype responses. These can result in specific inactivation and/or the rapid clearance of the drug.

Early data on the utility of chimeric antibodies (Morrison, 1984) in which the coding sequences for the variable region of the mAb are retained while the coding sequences for the constant regions are derived from human antibody, suggests that the HAMA response may indeed be reduced; however, a HAMA response to the murine variable region may still emerge (reviewed by Adair (Adair, 1992)) and more recently the humanization process has been taken further by substituting into a human antibody those amino acids in the variable regions believed to be involved in antigen binding to give a fully humanized antibody (Reichman, 1988).

A major concern is that the humanized antibody will still be immunogenic because of the presence of the non-CDR residues which need to be transferred in order to regenerate suitable antigen binding activity, in addition to any anti-paratope antibodies that may be generated. To date two humanized antibodies, CAMPATH-1H and Hu2PLAP, have been administered to patients (LoBuglio, 1989). Both of these antibodies used the rodent amino acid sequences in complementarity determining regions (CDRs) as defined by Kabat (1987), along with the rodent framework residues at position 27, where the amino acid is buried, and position 30 where the residue is predicted to be solvent accessible near CDR1. In both cases no specific immune response to initial treatments with the administered antibody was noted, although responses to a second course of treatment was seen in one study using CAMPATH-1H for the treatment of rheumatoid arthritis (Frenken, 1991). There have been no reported clinical studies using humanized antibodies in which other non-CDR solvent-accessible residues have also been included in the design.

The interactions of various cell surface proteins such as T-cell receptor/CD3 complex (TCR/CD3), MHC, CD8, ED45 and CD4 have been shown to be important in the stimulation of T-cell responses (Floury, 1991, Swartz, 1985, Strominger, 1980, Weiss, 1988). Two of these molecules, CD4 and CD3 have been found to be physically associated on the T-cell (Saizawa, 1987, Anderson, 1988, Rojo, 1989, Mittler, 1989, Dianzani, 1992). This association is critical to T-cell receptor mediated signal transduction, in part due to their associated kinase and phosphatase activities (Ledbetter, 1990). Molecules which can interrupt or prevent these interactions (i.e. antibodies) are currently recognized as therapeutically useful in the treatment of kidney allograft rejection (Ortho Multi Center Transplant Group, 1985). A modification of antibody treatment, one in which several of the T-cell surface proteins are directly bound together by one antibody might prove useful in current immunotherapy protocols. In addition to blocking cell adhesion or cell to cell interaction, antibodies which are capable of cross-linking several cell surface proteins may result in stimulation of T-cell activity or induction of aberrant signalling, and thus produce modulation of the immune response (Ledbetter, 1990).

Bringing together molecules involved in T-cell activation such as CD3 and CD4, or CD3 and CD8, may be a potent method for immunoactivation. Previous studies have shown that cross-linking CD3 and CD4 with heteroconjugates composed of anti-CD3 and anti-CD4 antibodies result in a greater stimulation of $Ca^{2+}$ flux than that observed with CD3 cross-linked to itself or simultaneous cross-linking of CD3 and CD4 by separate reagents (Ledbetter, 1990). Similarly, cross-linking CD3 and CD8 with immobilized antibody mixtures resulted in synergistic effects on T-cell proliferation and interleukin 2 (IL-2) receptor expression (Emmrich, 1986 and 1987). These studies taken together point to a critical role for the interaction of CD3 with CD4/8 in T-cell activation.

The immunomodulatory effect of cross linking various T-cell surface molecules can be both immunosuppressive and immunostimulatory. Linkage of CD4 with itself or other T-cell surface molecules has been shown to result in a different pattern of protein phosphorylation compared to cross-linking CD3 to itself (Ledbetter, 1990). This aberrant signalling may result as a consequence of binding both CD3 and CD4 simultaneously by a single cross-linking reagent. Previous studies have shown that pretreatment of T-cells with antibody to cross-link CD4 to itself before anti-CD3 treatment inhibits T-cell activation and promotes apoptosis (Newell, 1990). These results would argue that a reagent that crosslinks CD4 with CD3, or other T-cell surface molecules, could be a potent immunosuppressant by virtue of inappropriate signalling through the TCR/CD3 complex.

BRIEF SUMMARY OF THE INVENTION

In one embodiment, the present invention contemplates a "humanized" version of the murine OKT3 antibody, a powerful immunosuppressive agent. In a preferred embodiment, the "humanized" monoclonal antibody of the present invention comprises a point mutation to leucine at position 234. In another embodiment, the antibody of the present invention comprises a point mutation to glutamic acid at position 235.

BRIEF DESCRIPTION OF THE DRAWINGS

In the drawings, which form a portion of the specification:
FIG. 1A and FIG. 1B. Sequences of humanized OKT3 variable regions. FIG. 1A and FIG. 1B show the alignments of the OKT3 light chain (FIG. 1A), SEQ ID NO: 6, and the heavy chain (FIG. 1B), SEQ ID NO: 10, variable domain amino acid sequence (row 1), the variable domain sequence from the human antibodies chosen as acceptor framework (row 2), SEQ ID NOS: 7 and 11, and the humanized OKT3 variable domain sequences (row's 3–5), SEQ ID NOS: 8, 9, 12, 13, and 14. The CDR choices are singly underlined. Rows 3–5 (SEQ ID NOS: 8, 9, 12, 13, and 14) show only differences from the human acceptor sequence, with the non-CDR differences shown double underlined. Dashes indicate gaps introduced in the sequences to maximize the alignment. Numbering is as Kabat (1987).

FIG. 2A, FIG. 2B, FIG. 2C, FIG. 2D, FIG. 2E, FIG. 2F, FIG. 2G, FIG. 2H, FIG. 2I, FIG. 2J, and FIG. 2K Amino acid and nucleotide sequence of murine OKT3.

FIG. 3A and FIG. 3B show results from separate experiments. solid squares: Orthomune® OKT3; open circles: cOKT3(γ4); closed triangles: gDKT3-1(γ4); closed circles: gOKT3-5(γ4); open squares: gOKT3-7(γ4); open triangles: mOKT4A.

FIG. 6. N-terminal region of $CH_2$ domain.

DETAILED DESCRIPTION OF THE INVENTION

I. The Invention

Figure 3A:
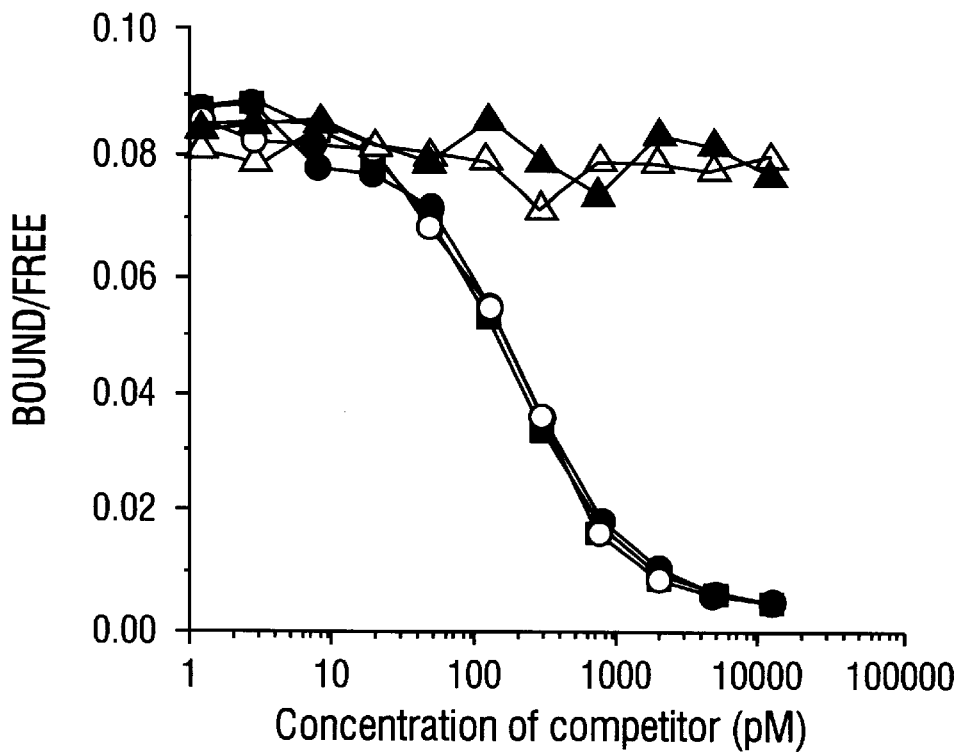
FIG. 3A and FIG. 3B. Relative Affinity Determination. Competition of OKT3 and humanized OKT3 antibodies for antigen against FITC-mOKT3. Increasing concentrations of unlabelled competitor antibody were added to a subsaturating concentration of FITC-mOKT3 tracer antibody, and were incubated with human PBMC for 1 hour at 4° C. Cells were washed and fixed, and the amount of bound and free FITC-mOKT3 was calculated. The affinities of the antibodies were each calculated according to the formula [X]–[mOKTK3]=$(1/K_x)-(1/K_a)$, where $K_a$ is the affinity of mOKT3, and Kx is the affinity of the competitor X. [ ] indicates the concentration of competitor at which bound/free tracer binding is $R_o/2$ and $R_o$ is maximal tracer binding (Rao, 1992).

The potent immunosuppressive agent OKT3 is a murine IgG2a mAb directed against the CD3 complex associated with the human TCR (Van Wauwe, 1980). However, the administration of OKT3 to transplant recipients induces the systematic release of several cytokines, including IL-2, IL-6, TNF-α and IFN-γ (Abramowicz, 1989; Chatenoud, 1989). This production of cytokines has been correlated with the adverse side-effects frequently observed after the first injection of OKT3 (Van Wauwe, 1980; Chatenoud, 1989; Thistlethwaite, 1988), and may augment the production of anti-isotopic and anti-idiotypic antibodies occurring in some patients after one or two weeks of treatment, that can neutralize OKT3 and preclude subsequent treatments of rejection episodes (Thistlethwaite, 1988).

Several pieces of evidence strongly suggest that these side-effects are a consequence of the cross-linking between T lymphocytes and Fc receptor (FcR)-bearing cells through the Fc portion of OKT3, resulting in activation of both cell types (Debets, 1990; Krutman, 1990): 1.) anti-CD3 mAbs did not stimulate T-cell proliferation in vitro, unless the Ab was immobilized to plastic or bound to FCR+ antigen presenting cells included in the culture (van Lier, 1989); 2.) the cross-linking of OKT3 through FcRs I and II enhanced proliferation in response to IL-2, in vitro (van Lier, 1987); 3.) proliferation of murine T-cells induced by 145-2C 11, a hamster mAb directed against the murine CD3 complex, could be blocked by the anti-FcR Ab, 2.4G2; 4.) the injection into mice of F(ab')$_2$ fragments of 145-2C11 induced significant immunosuppression without triggering full T-cell activation (Hirsch, 1990) and was less toxic in mice than the whole mAb (Allegre, 1990); 5.) the administration of an OKT3 IgA switch variant that displayed a reduced FcR-mediated T-cell activation as compared with OKT3 IgG2a, resulted in fewer side effects in chimpanzees in vivo (Parleviet, 1990).

Thus, theoretically, improvement of anti-CD3 mAb therapy can be obtained by molecularly modifying OKT3 to reduce its affinity for FcRs. The mutated Ab obtained would lead to lower cellular activation and acute toxicity in vivo, but conserved immunosuppressive properties.

II. The Immune System

The immune system of both humans and animals include two principal classes of lymphocytes: the thymus derived cells (T-cells), and the bone marrow derived cells (B cells). Mature T-cells emerge from the thymus and circulate between the tissues, lymphatics, and the bloodstream. T-cells exhibit immunological specificity and are directly involved in cell-mediated immune responses (such as graft rejection). T-cells act against or in response to a variety of foreign structures (antigens). In many instances these foreign antigens are expressed on host-cells as a result of infection. However, foreign antigens can also come from the host having been altered by neoplasia or infection. Although T-cells do not themselves secrete antibodies, they are usually required for antibody secretion by the second class of lymphocytes, B cells.

A. T-cells

There are various subsets of T-cells, which are generally defined by antigenic determinants found on their cell surfaces, as well as functional activity and foreign antigen recognition. Some subsets of T-cells, such as $CD8^+$ cells, are killer/suppressor cells that play a regulating function in the immune system, while others, such as $CD4^+$ cells, serve to promote inflammatory and humoral responses. (CD refers to cell differentiation cluster; the accompanying numbers are provided in accordance with terminology set forth by the International Workshops on Leukocyte Differentiation, *Immunology Today,* 10:254 (1989). A general reference for all aspects of the immune system may be found in Klein, J. (1982).

1. T-cell activation

Human peripheral T lymphocytes can be stimulated to undergo mitosis by a variety of agents including foreign antigens, monoclonal antibodies and lectins such as phytohemagglutinin and concanavalin A. Although activation presumably occurs by binding of the mitogens to specific sites on cell membranes, the nature of these receptors, and their mechanism of activation, is not completely elucidated. Induction of proliferation is only one indication of T-cell activation. Other indications of activation, defined as alterations in the basal or resting state of the cell, include increased lymphokine production and cytotoxic cell activity.

T-cell activation is an unexpectedly complex phenomenon that depends on the participation of a variety of cell surface molecules expressed on the responding T-cell population (Leo, 1987; Weiss, 1984). For example, the antigen-specific T-cell receptor (TcR) is composed of a disulfide-linked heterodimer, containing two clonally distributed, integral membrane glycoprotein chains, α and β, or γ and δ, non-covalently associated with a complex of low molecular weight invariant proteins, commonly designated as CD3 (the older terminology is T3 (Leo, 1987)).

The TcR α and β chains determine antigen specificities (Saito, 1987). The CD3 structures are thought to represent accessory molecules that may be the transducing elements of activation signals initiated upon binding of the TcR αβ to its ligand. There are both constant regions of the glycoprotein chains of TcR, and variable regions (polymorphisms). Polymorphic TcR variable regions define subsets of T-cells, with distinct specificities. Unlike antibodies which recognize soluble whole foreign proteins as antigen, the TcR complex interacts with small peptidic antigen presented in the context of major histocompatibility complex (MHC) proteins. The MHC proteins represent another highly polymorphic set of molecules randomly dispersed throughout the species. Thus, activation usually requires the tripartite interaction of the TcR and foreign peptidic antigen bound to the MHC proteins.

With regard to foreign antigen recognition by T-cells, the number of peptides that are present in sufficient quantities to bind both the polymorphic MHC and be recognized by a given T-cell receptor, thus inducing immune response as a practical mechanism, is small. One of the major problems in clinical immunology is that the polymorphic antigens of the MHC impose severe restrictions on triggering an immune response. Another problem is that doses of an invading antigen may be too low to trigger an immune response. By the time the antigenic level rises, it may be too late for the immune system to save the organism.

The tremendous heterogeneity of the MHC proteins among individuals remains the most serious limiting factor in the clinical application of allograft transplantation. The ability to find two individuals whose MHC is identical is extremely rare. Thus, T-cells from transplant recipients invariably recognize the donor organ as foreign. Attempts to suppress the alloreactivity by drugs or irradiation has resulted in severe side effects that limit their usefulness. Therefore, more recent experimental and clinical studies have involved the use of antibody therapy to alter immune function in vivo. The first successful attempt to develop a more selective immunosuppressive therapy in many was the use of polyclonal heterologous anti-lymphocyte antisera (ATG) (Starzl, 1967; Shield, 1979).

2. Antibody structure

Antibodies comprise a large family of glycoproteins with common structural features. An antibody is comprised of four polypeptides that form a three dimensional structure which resembles the letter Y. Typically, an antibody is comprised of two different polypeptides, the heavy chain and the light chain.

An antibody molecule typically consists of three functional domains: the Fc, Fab, and antigen binding site. The Fc domain is located at the base of the Y. The arms of the Y comprise the Fab domains. The antigen binding site is located at the end of each arm of the Y.

There are five different types of heavy chain polypeptides which types are designated $\alpha$, $\delta$, $\epsilon$, $\gamma$, and $\mu$. There are two different types of light chain polypeptides designated k and $\lambda$. An antibody typically contains only one type of heavy chain and only one type of light chain, although any light chain can associate with any heavy chain.

Antibody molecules are categorized into five classes, IgG, IgM, IgA, IgE and IgD. An antibody molecule comprises one or more Y-units, each Y comprising two heavy chains and two light chains. For example IgG consists of a single Y-unit and has the formula $\gamma_2 k_2$ or $\gamma_2 \lambda_2$. IgM is comprised of 5 Y-like units.

The amino terminal of each heavy and light chain polypeptide is known as the constant (C) region. The carboxyl terminal of each heavy and light chain polypeptide is known as the variable (V) region. Within the variable regions of the chains are Hypervariable regions known as the complementarity determining regions (CDR). The variable regions of one heavy chain and one light chain associate to form an antigen binding site. Each heavy chain and each light chain includes three CDRs. The six CDRs of an antigen binding site define the amino acid residues that form the actual binding site for the antigen. The variability of the CDRs account for the diversity of antigen recognition.

B. Immune Response

The principal function of the immune system is to protect animals from infectious organisms and from their toxic products. This system has evolved a powerful range of mechanisms to locate foreign cells, viruses, or macromolecules; to neutralize these invaders; and to eliminate them from the body. This surveillance is performed by proteins and cells that circulate throughout the body. Many different mechanisms constitute this surveillance, and they can be divided into two broad categories—nonadaptive and adaptive immunity.

Adaptive immunity is directed against specific molecules and is enhanced by re-exposure. Adaptive immunity is mediated by cells called lymphocytes, which synthesize cell-surface receptors or secrete proteins that bind specifically to foreign molecules. These secreted proteins are known as antibodies. Any molecule that can bind to an antibody is known as an antigen. When a molecule is used to induce an adaptive response it is called an immunogen. The terms "antigen" and "immunogen" are used to describe different properties of a molecule. Immunogenicity is not an intrinsic property of any molecule, but is defined only by its ability to induce an adaptive response. Antigenicity also is not an intrinsic property of a molecule, but is defined by its ability to be bound by an antibody.

The term "immunoglobulin" is often used interchangeably with "antibody." Formally, an antibody is a molecule that binds to a known antigen, while immunoglobulin refers to this group of proteins irrespective of whether or not their binding target is known. This distinction is trivial and the terms are used interchangeably.

Many types of lymphocytes with different functions have been identified. Most of the cellular functions of the immune system can be described by grouping lymphocytes into three basic types—B cells, cytotoxic T-cells, and helper T-cells. All three carry cell-surface receptors that can bind antigens. B cells secrete antibodies, and carry a modified form of the same antibody on their surface, where it acts as a receptor for antigens. Cytotoxic T-cells lyse foreign or infected cells, and they bind to these target-cells through their surface antigen receptor, known as the T-cell receptor. Helper T-cells play a key regulatory role in controlling the response of B cells and cytotoxic T-cells, and they also have T-cell receptors on their surface.

The immune system is challenged constantly by an enormous is number of antigens. One of the key features of the immune system is that it can synthesize a vast repertoire of antibodies and cell-surface receptors, each with a different antigen binding site. The binding of the antibodies and T-cell receptors to foreign molecules provides the molecular basis for the specificity of the immune response.

The specificity of the immune response is controlled by a simple mechanism—one cell recognizes one antigen because all of the antigen receptors on a single lymphocyte are identical. This is true for both T and B lymphocytes, even though the types of responses made by these cells are different.

All antigen receptors are glycoproteins found on the surface of mature lymphocytes. Somatic recombination, mutation, and other mechanisms generate more than $10^7$ different binding sites, and antigen specificity is maintained by processes that ensure that only one type of receptor is synthesized within any one cell. The production of antigen receptors occurs in the absence of antigen. Therefore, a diverse repertoire of antigen receptors is available before antigen is seen.

Although they share similar structural features, the surface antibodies on B cells and the T-cell receptors found on T-cells are encoded by separate gene families; their expression is cell-type specific. The surface antibodies on B cells can bind to soluble antigens, while the T-cell receptors recognize antigens only when displayed on the surface of other cells.

When B-cell surface antibodies bind antigen, the B lymphocyte is activated to secrete antibody and is stimulated to proliferate. T-cells respond in a similar fashion. This burst of cell division increases the number of antigen-specific lymphocytes, and this clonal expansion is the first step in the development of an effective immune response. As long as the antigen persists, the activation of lymphocytes continues, thus increasing the strength of the immune response. After the antigen has been eliminated, some cells from the expanded pools of antigen-specific lymphocytes remain in circulation. These cells are primed to respond to any subsequent exposure to the same antigen, providing the cellular basis for immunological memory.

In the first step in mounting an immune response the antigen is engulfed by an antigen presenting cell (APC). The APC degrades the antigen and pieces of the antigen are presented on the cell surface by a glycoprotein known as the major histocompatibility complex class II proteins (MHC II). Helper T-cells bind to the APC by recognizing the antigen and the class II protein. The protein on the T-cell which is responsible for recognizing the antigen and the class II protein is the T-cell receptor (TCR).

Once the T-cell binds to the APC, in response to Interleukins I and II (IL-1 and IL-2), helper T-cells proliferate exponentially. In a similar mechanism, B cells respond to an antigen and proliferate in the immune response.

The TCR acts in conjunction with a protein that is also expressed on the surface of the T-cell called CD3. The complex is the TCR-CD3 complex. Depending on the type of lymphocyte, the lymphocyte can also express other cell surface proteins which include CD2, CD4, CD8, and CD45. The interactions between these cell surface proteins are important in the stimulation of T-cell response.

Two major sub-populations of T-cells have been identified. CD4 lymphocytes can present on their cell surface the CD4 protein, CD3, and their respective T-cell receptors. CD8 lymphocytes can present on their cell surface the CD8 protein, CD3 and its respective T-cell receptor.

CD4 lymphocytes generally include the T-helper and T-delayed type hypersensitivity subsets. The CD4 protein typically interacts with Class II major histocompatibility complex. CD4 may function to increase the avidity between the T-cell and its MHC class II APC or stimulator cell, and enhance T-cell proliferation.

CD8 lymphocytes are generally cytotoxic T-cells, whose function is to identify and kill foreign cells or host-cells displaying foreign antigens. The CD8 protein typically interacts with Class I major histocompatibility complex.

C. Clinical use of antibodies

Clinical trials of the ATG treatment suggested a significant reduction of early rejection episodes, improved long term survival and, most importantly, reversal of ongoing rejection episodes. However, the results were often inconsistent due to the inability to standardize individual preparations of antisera. In addition, the precise nature of the target antigens recognized by the polyclonal reagents could not be defined, thus making scientific analysis difficult. The advent of monoclonal antibody (mAb) technology provided the bases for developing potentially therapeutic reagents that react with specific cell surface antigens which are involved in T-cell activation.

One of the clinically successful uses of monoclonal antibodies is to suppress the immune system, thus enhancing the efficacy of organ or tissue transplantation. U.S. Pat. No. 4,658,019, describes a novel hybridoma (designated OKT3) which is capable of producing a monoclonal antibody against an antigen found on essentially all normal human peripheral T-cells. This antibody is said to be monospecific for a single determinant on these T-cells, and does not react with other normal peripheral blood lymphoid cells. The OKT3 mAb described in this patent is currently employed to prevent renal transplant rejection (Goldstein, 1987).

One unexpected side effect of the OKT3 therapy was the profound mitogenic effect of the mAb in vivo (Ellenhorn, 1988).

In addition, other cell surface molecules have been identified that can activate T-cell function, but are not necessarily part of the T-cell surface receptor complex. Monoclonal antibodies against Thy-1, TAP, Ly-6, CD2, or CD28 molecules can activate T-cells in the absence of foreign antigen in vitro (Leo, 1989; Takada, 1984). Moreover, certain bacterial proteins although differing in structure from mAbs, also have been shown to bind to subsets of T-cells and activate them in vitro (White, 1989).

The possibility of selectively down-regulating the host's immune response to a given antigen represents one of the most formidable challenges of modern immunology in relation to the development of new therapies for IgE-mediated allergies, autoimmune diseases, and the prevention of immune rejection of organ transplants. Similar considerations apply to an increasing number of promising therapeutic modalities for a broad spectrum of diseases, which would involve the use of foreign biologically active agents potentially capable of modulating the immune response, provided they were not also immunogenic. Among these agents, one may cite xenogeneic monoclonal or polyclonal antibodies (collectively referred to here as xIg) against different epitopes of the patients' $CD4^+$ cells (Cruse, 1989; Diamantstein 1986), administered alone or in combination with immunosuppressive drugs for the treatment of rheumatoid arthritis and other autoimmune diseases, or for the suppression of graft-versus-host reactions and the immune rejection of organ transplants (Cruse, 1989).

The therapeutic effectiveness of these immunological strategies is undermined by the patients' antibodies which prevent these molecules from reaching their target-cells. In addition, the repeated administration of these agents may result in serious complications, viz. serum sickness, anaphylactic symptoms (i.e. bronchospasm, dyspnea and hypotension) and/or the deposition in the liver of toxic immune complexes leading frequently to hepatotoxicity.

D. Preparation of monoclonal and polyclonal antibodies

Briefly, a polyclonal antibody is prepared by immunizing an animal with an immunogen, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used for the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various points following immunization. When a desired level of immunogenicity is obtained, the immunized animal can be bled and the serum isolated and stored.

A monoclonal antibody of the present invention can be readily prepared through use of well-known techniques such as those exemplified in U.S. Pat. No 4,196,265, herein incorporated by reference. Typically, a technique involves first immunizing a suitable animal with a selected antigen in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce a monoclonal antibody, mice are injected intraperitoneally with between about 1–200 µg of an antigen. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

III. Immunusuppressive modulation through use of "humanized" mAbs

In order to improve the effectiveness and expand the uses of OKT3, humanized versions of the antibody have been generated. It has been shown (Woodle, 1992) that simple transfer of the loop regions and the complementarity determining regions (Kabat, 1987), which are believed to contain the antigen-contacting amino acids, into a human framework was not sufficient in the case of OKT3 to provide the structure required for efficient antigen binding. Examination of the remaining framework residues identified several which could potentially contribute to a reconstitution of binding in a human framework. When amino acids at these positions in the human framework were replaced with those from OKT3 to give gOKT3-5, antigen binding was shown to be fully restored. Subsequently, it has been noted that a number of these amino acids derived from the OKT3 sequence are not required to achieve a humanized antibody with the same affinity as murine OKT3.

To reduce the immune responses observed in patients treated with murine OKT3, a "humanized" OKT3 (gOKT3-5), comprised of the complementary determining regions (CDR) of the murine anti-CD3 mAb and of the variable framework and constant regions of a human IgG4, was developed. However, as a therapeutic drug, an additional problem associated with OKT3, the first-dose reactions attributed to the T-cell activation by the mAb, remained. Since gOKT3-5 produces, in vitro, similar activation to OKT3, it is quite likely that the same side-effects might also occur with this drug in vivo. $F(ab')_2$ fragments of OKT3 have led to potent immunosuppression and TCR modulation, in vitro. Non-activating $F(ab')_2$ fragments of anti-CD3 mAbs to mice was as efficacious as whole anti-CD3 in delaying skin graft rejection, while the $F(ab')_2$ fragments exhibited significantly reduced T-cell activation and fewer side-effects in mice. However, the production of $F(ab')_2$ fragments in large quantities remains difficult. Furthermore, the half-life of this drug in the blood stream is relatively short, as compared with whole mAb. Thus, frequent injections of the $F(ab')_2$ fragments of anti-CD3 were necessary to achieve maximal immunosuppression, making the use of this mAb fragment inappropriate for clinical transplantation. Finally, recent studies have shown that even a small contaminant of whole mAb in the $F(ab')_2$ preparation ($<1/10^4$ molecules) has a synergistic effect on T-cell activation.

A. Point mutations in "humanized" mAbs

The Fc portion of the murine IgG2a Abs, including OKT3, binds preferentially to the high affinity 72 kD FcR I (CD64) present on human macrophages and IFN-γ- stimulated polymorphonuclear leukocytes (Anderson, 1986; Lynch, 1990; Shen, 1987), but also to the low affinity 40 kD FcR II (CD32) that is found on human macrophages, β cells and polymorphonuclear neutrophils (Anderson, 1986; Petroni, 1988; Bentin, 1991). The CH2 region in the Fc portion of IgGs has been found to be the domain that selectively binds FcR I and II (Ollo, 1983; Woof, 1984; Burton, 1985; Partridge, 1986; Duncan, 1988). In fact, the exact binding segment has been localized to an area corresponding to amino acids 234 to 238 (Duncan, 1988) and the respective affinity of several isotypes has been determined (Gergely, 1990). Duncan et al. have shown that the mutation of a single amino acid in the FcR binding segment of a murine IgG2b, converting the sequence to that found in a murine IgG2a, resulted in a 100-fold enhancement of the binding to FcR (1988).

Based on those data, a mutation was introduced into the Fc region of an anti-CD3 human IgG4 antibody resulting in a sequence similar to the low affinity sequence of the murine IgG2b. This mAb contains a glutamic acid rather than a leucine at position 235 of the human IgG4 heavy chain (Glu-235 mAb). The mutational analysis was performed on a "humanized" anti-CD3 mAb, the gOKT3-5 mAb constructed by splicing the murine complementary determining regions into the human IgG4 framework gene sequence. The gOKT3-5 mAb was previously shown to retain binding affinity for the CD3 complex similar to murine OKT3 and all the in vitro activation and immunosuppressive properties of OKT3. In addition, the gOKT3-5 mAb had an FcR binding sequence differing by only two amino acids from the same region on the murine IgG2b or by one amino acid in the murine IgG2a/human IgG1. Since a mutation in the FcR binding region of the mAb could modify the conformation of the molecule and thus be responsible for a decrease in FcR binding regardless of the amino acid sequence obtained, we performed a control mutation of amino acid 234 from a phenylalanine into a leucine in order to mimic the FcR binding area found in the high affinity murine IgG2a and human IgG1. This mAb was designated Leu-234.

Therefore, the site-specific mutations described above were introduced into the Fc portion of the gOKT3-5 mAb to affect the binding of the Ab to FcR. The appropriate mutant of the anti-CD3 mAb was designed to exhibit the low-activating properties of F(ab')$_2$ fragments, the purity of a monoclonal antibody and an increased serum half-life as compared with F(ab')$_2$ fragments or possibly even with murine OKT3, since chimeric mouse/human antibodies have been shown to circulate longer than their murine counterpart. The resulting mAb thus avoids the acute toxicity and the immunization induced by OKT3, in vivo, although, theoretically, the substitution of glutamic acid at position 235 in order to mimic murine IgG2b could also create an immunogenic epitope in the constant region of the humanized antibody.

In fact, a single amino acid substitution of a glutamic acid for a leucine at position 235 in the Fc portion of the gOKT3-5 mAb resulted in a mAb which bound U937 cells 100-fold less than the murine OKT3. This mutation, which generated an FcR I binding sequence similar to the one found in murine IgG2b, resulted in a mAb with a 10-fold lower affinity for FcR than the murine IgG2b. The reason for this difference is unclear but may imply that the interaction of the five amino acid-FcR binding region with the adjacent amino acids, which in the case of the Glu mAb are part of a human IgG4, is relevant to FcR binding.

All the Abs tested showed some modulation of the TCR after a culture of 12 hours. However, the Glu-235 mAb had to be added in higher concentrations or for a longer period of time to achieve maximal modulation. This suggests that low FcR binding might delay the induction of TCR internalization. All the Abs also inhibited CTL activity, indicating similar suppressive properties by this assay. Thus, altering the binding of the gOKT3-5 mAb by site-directed mutagenesis did not significantly affect the immunosuppressive ability of the mAb, in vitro.

The reduced binding of the Glu-235 mAb to FcR I correlated with a marked decrease in the T-cell activation induced by this Ab, as assessed by the absence of T-cell proliferation, the decreased expression of cell surface markers of activation, the diminished release of TNF-α and GM-CSF, and the lack of secretion of IFN-γ. The magnitude of T-cell mitogenesis is known to correlate with the affinity of anti-CD3 mAbs for FcR I, whose relative binding is IgG1=IgG3>IgG4 for human subclasses of Abs and IgG2a=IgG3>IgG1>IgG2b for murine isotypes. The anti-CD3 mAbs employed in this study displayed an FcR binding as expected, with the human IgG4 gOKT3-5 mAb binding less avidly to U937 cells than murine IgG2a OKT3 or Leu-234 mAb, but with much higher affinity than the Glu-235 mAb.

The activation induced by the different anti-CD3 mAbs tested did not entirely correlate with their affinity for FcRs. In spite of the increased affinity of OKT3 for FcRs as compared with the gOKT3-5 mAb, no significant difference in the T-cell activation was observed between the two mAbs. One explanation could be that activation is maximal whenever a certain threshold of cross-linking between T lymphocytes and FcR is attained. Another possibility is that the binding of the mAb to the CD3 antigen potentiates its avidity for FcR-bearing cells.

The extent of the functional changes generated in the FcR binding region of the gOKT3-5 mAb that form the Glu-235 mAb has further implications. The ability of certain isotypes of anti-CD3 mAbs to activate T-cells and mediate ADCC has been shown to vary in the population. Murine IgG2a and IgG3 anti-CD3 mAbs are mitogenic for virtually all individuals. In contrast, murine IgG1 and IgG2b mAbs induce proliferation in only 70% and 5% to 10%, respectively. However, even in these individuals, IgG2b mAbs seem to trigger a different pathway of activation. For instance, in contrast to other anti-CD3 isotypes, IgG2b mAbs do not induce the production of IL-2 or IFN-γ. Thus, the proliferation observed in the small subset of the patient population may be an IL-2 independent T-cell mitogenesis, which has previously been reported in other settings. More importantly, the reduced FcR binding of the Glu-235 mAb to FcR, as compared with murine IgG2b Abs, may be sufficient to abrogate the activation of even this subset of individuals.

In one embodiment, the present invention contemplates a class of homo-bifunctional antibodies, a humanized version of OKT3 which also interacts with CD4. This humanized antibody has an Fv region containing the CD3 ε antigen specificity of OKT3 and an Fc region from either human IgG1 or IgG4 antibody. The humanized-anti-CD3 antibody binds CD4 directly, either immobilized on plastic or on CD4$^+$, CD3$^-$, FcR I cells. Initial mapping experiments suggest that the binding occurs near the OKT4A epitope on CD4. The weak interaction of some antibodies (but not human IgG4) with this region of CD4, independent of antigen/antibody binding site, has been reported (Lanert, 1991). However, unlike these reports, the antibody of the present invention binds with either a γ1 or a γ4 heavy chain. The CD4 binding site on humanized OKT3 has been mapped to the Fab fragment and probably resides in the framework sequences of the variable region.

VII. Pharmaceutical Compositions

In a preferred embodiment, the present invention provides pharmaceutical compositions comprising antibodies immunoreactive with CD3 and CD4 cell surface antigens.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g., Gabizon et al., 1990; Ferruti et al., 1986; and Ranade, V. V., 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1
Mutation in the Fc portion of the human-OKT3 mAb

Mutations of the phenylalanine in position 234 into a leucine to increase the affinity of the binding of the mAb to FcR I (Leu-234), or of the contiguous leucine (235) into a glutamic acid to reduce FcR binding (Glu-235) were performed as follows: ultracompetent CJ 236 E. coli (Invitrogen, San Diego, Calif.) were transformed with pSG5 containing the heavy chain gene of the gOKT3 mAb. The bacteria were allowed to grow in LB broth supplemented with uridine (25 mg/mL), ampicillin (100 µg/mL) until reaching an optical density of 0.35 at a wavelength of 600 nm. The CJ 236 E. coli were infected with helper phage M-13 (Stratagen) to generate uridine incorporated single stranded template. An oligonucleotide synthesized with thymidine and containing the desired mutation was then annealed to the uridine-single-stranded template to serve as a primer for the replication of the plasmid after the addition of deoxynucleotides, T7 polymerase and T4 ligase; the wild type DNA thus contains uridine, while the mutated plasmid obtained utilizes thymidine. The synthesis reaction was stopped with EDTA 0.5M and Tris HCl-EDTA 1M, and 10 µl were transformed into competent DH5 E. coli that degrade uridine-DNA and thus grew on ampicillin-selected media when transformed with the mutated construct. The plasmid was isolated by Qiagen minipreps; the mutated sequence in pSG5 was co-introduced with the psG5 vector containing the light chain of the mAb into COS-1 cells for transient expression of the mutant immunoglobulin.

Example 2
Generation and identification of OKT3 variable region sequences

OKT3 variable region sequences were derived from oligo-dT primed cDNA from OKT3 hybridoma cells using the Amersham International Plc. cDNA synthesis kit. The cDNA was cloned in pSP64 using EcoR1 linkers. E. coli clones containing light and heavy chain cDNAs were identified by oligonucleotide screening of bacterial colonies using the oligonucleotides: 5' TCCAGATGTTAACTGCT-CAC (SEQ ID NO: 15) for the light chain, which is complementary to a sequence in the mouse kappa constant region, and 5' CAGGGGCCAGTGGATGGATAGAC (SEQ ID NO: 16) for the heavy chain, which is complementary to a sequence in the mouse igG2a constant CH1 domain region.

The amino acid sequences for the variable regions deduced from the sequences of the cDNAs are shown in FIG. 1A (row 1), SEQ ID NO: 6, for the light chain and FIG. 1B (row 1), SEQ ID NO: 10, for the heavy chain. The CDR's are shown with the single underlining. The light chain is a member of the mouse $V_L$ subgroup VI and uses a $J_K4$ minigene. The heavy chain is probably a member of the mouse $V_H$ subgroup II, most probably IIb, although it also has significant homology to the consensus for group Va. The D region is currently unclassified and the $J_H$ region is $J_H2$. In terms of the loop predictions for the hypervariable regions proposed by Chothia et al., (1987), the loops can be assigned to canonical structures 1 for L1, 2 for L2 and 1 for L3, and to canonical structures 1 for H1 and 2 for H2; Chothia et al., have not yet predicted canonical forms for H3.

The light chain variable region amino acid sequence shows a high degree of homology to the Ox-1 germline gene and to the published antibodies 45.2.21.1, 14.6b.1 and 26.4.1 (Sikder, 1985). The heavy chain variable region amino acid sequence shows reasonable homology to a subgroup of the J558 family including 14.6b.1. Some antibodies with these combinations of light and heavy chain genes have previously been shown to have affinity for alpha-1-6 dextran.

Example 3
Design and construction of humanized OKT3 genes

The variable region domains for the humanized antibodies were designed with mouse variable region optimal codon usage (Adair, 1992) and used the signal sequences of the light and heavy chains of mAb B72.3 (Whittle, 1987). Immediately 5' to the initiator ATG a 9 bp Kozak sequence (Kozak, 1987), GCCGCCACC (SEQ ID NO: 17), was inserted. 5' and 3' terminal restriction sites were added so that the variable regions could be attached directly to the DNA sequences for the human IgG4 and Kappa constant regions prior to cloning into the eukaryotic expression vectors.

The variable regions were built either by simultaneously replacing all of the CDR and loop regions by oligonucleotide-directed, site-specific mutagenesis (Ollo, 1983) of a previously constructed humanized variable region for B72.3 cloned in M13 (Emtage et al.), or by assembling the sequence using synthetic oligonucleotides ranging in size from 27–67 base pairs and with 6 base overhangs. The oligonucleotides were synthesized on an Applied Biosystems Model 380B DNA Synthesizer and purified by HPLC. The oligonucleotides were enzymatically phosphorylated, paired, annealed, and then equimolar aliquots of each pair were mixed and ligated. The cloning sites were exposed by restriction digestion of the ligation mixture and the correctly sized fragments were identified and cloned directly into the expression vectors, 5' to the constant regions, prior to sequencing and expression.

For the design of the humanized OKT3 variable region sequences, REI (Kabat, 1987) was chosen as the human light chain framework, and KOL was chosen for heavy chain variable region. In both cases, antibodies were selected for which a structure had been determined by X-ray crystallography so that a structural examination of individual residues in the human variable region frameworks could be made. The variable region sequences of the human acceptor frameworks are shown in FIG. 1A and FIG. 1B (row 2), SEQ ID NOS: 7 and 11.

For comparison purposes, the amino acid and nucleotide sequences for murine OKT3 (SEQ ID NOS: 2–5, and 1), respectively, as obtained from *Sequences of Proteins of Immunbiological Interest* 4/e (1987), are provided in FIG. 2A, FIG. 2B, FIG. 2C, FIG. 2D, FIG. 2E, FIG. 2F, FIG. 2G, FIG. 2H, FIG. 2I, FIG. 2J, and FIG. 2K.

Row 3 in each of FIG. 1A (SEQ ID NO: 8) and FIG. 1B (SEQ ID NO: 12) shows the sequences for the variable regions of the initial design, gL and gH. Only differences from the human acceptor sequence are shown. For gL, the CDR choices were as suggested by Kabat et al., and no other non-CDR murine residues were used. For gH, the OKT3 CDR's, as suggested by reference to Kabat et al., were substituted into the KOL sequence along with the murine residues at positions 27, 28 and 30 which are normally bound in a loop region adjacent to CDR1 (Chothia, 1987; 1989). The importance of residue 27 as a determiner of antigen binding was shown by Riechmann et al., (Reichman, 1988) in the reconstitution of binding activity of the CAMPATH-1 antibody. The residues 28 and 30 are predicted to be at the surface of the antibody and near to CDR1. Residue 29 is the same in both KOL and OKT3 (FIG. 1B), and therefore does not require to be altered.

Figure 3B:
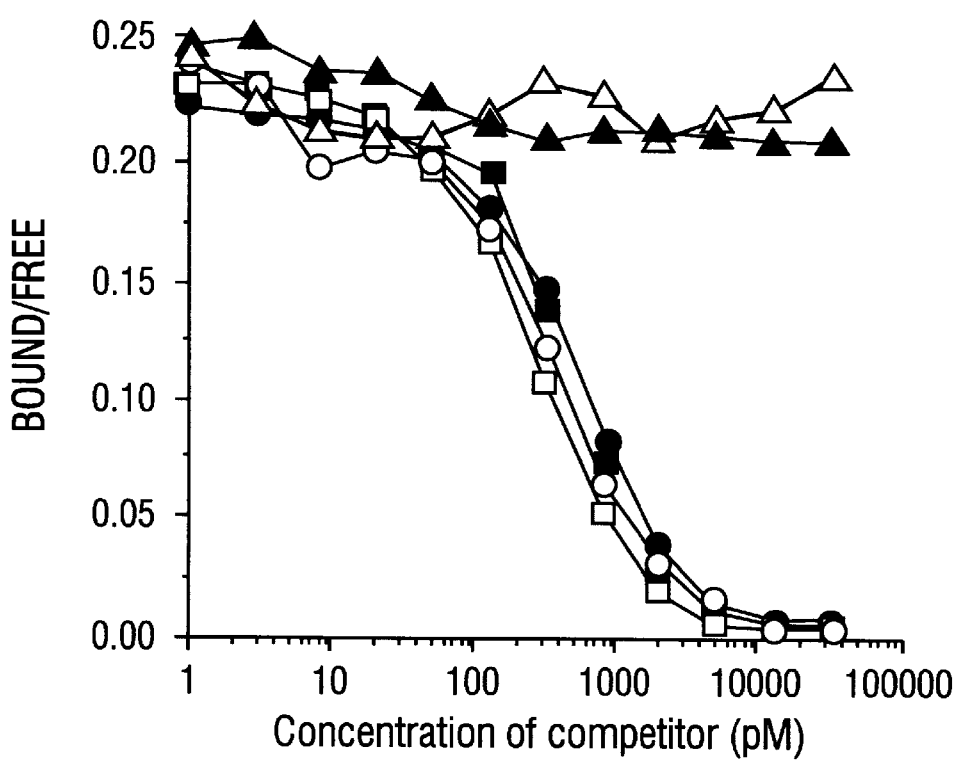

The DNA sequences coding for the initial humanized light and heavy variable regions were constructed by simultaneous replacement through site-directed mutagenesis of sequences in previously generated light and heavy chain DNAs of a humanized form of antibody B72.3. The DNA sequences coding for the humanized variable regions were then attached to the human gamma-4 and kappa constant region sequences and inserted into expression vectors as described for the chimeric genes. The gL and gH genes, when co-expressed in COS cells yield antibody gOKT3-1.

gOKT3-1 binds poorly to HPB-ALL cells and is not able to block the binding of mOKT3 to the cells (FIG. 3A and FIG. 3B). Therefore it was clear that further OKT3 residues outside of the CDRs needed to be considered for substitution into the humanized antibody. For the light chain these positions are at 1 and 3 which, by reference to known structures for antibody variable regions, are probable surface residues located near to the CDR's, residue 46 which is usually at the domain interface, and the packing residue at 47; gLA (SEQ ID NO:18) has all four residues derived from the murine sequence while gLC (SEQ ID NO:19) has murine residues at positions 46 and 47 only.

Similarly, for the heavy chain, a number of locations were considered. These were at positions 23, 73 and 76 which are believed, by analogy with known antibody structures, to be partly or completely solvent exposed residues near the CDRs; at positions 6, 24, 48, 49, 71, 78 and 88 which are residues believed either to be involved in positioning of the CDRs and/or in intradomain packing, and the variable domain interface residue 91. Finally at residue 63 in CDR2, which is usually an intra-domain packing residue, the residue found in KOL was used so that potentially unfavorable contacts with other packing residues from the human framework could be avoided. A number of light and heavy chain variants were built to assess the contribution of these framework residues. It was found by experiment that residues 1 and 3 on the light chain were not required to be derived from the murine sequence, but that one or both of residues 46 and 47 should be derived from the murine sequence. FIG. 1A, row 4 (SEQ ID NO: 9) shows the sequence of gLC which differs from gL by having the murine sequences at residues 46 and 47. Similarly, in the heavy chain it was found that while incorporating all of the modifications described above to give gHA (FIG. 1B row 4), SEQ ID NO: 13, and co-expressing this gene with cL or gLC would lead to antigen binding equivalent to cOKT3 or mOKT3, some of the residues were not necessary to retain equivalent binding affinity. In particular it was found when the KOL sequences were used at positions 71, 73, 76, 88 and 91 in the gHG gene, co-expression of gHG with cL or gLC led to antigen binding equivalent to cOKT3 or mOKT3. Therefore, the binding affinity of the gLC/gHA(gOKT3-5) and gLC/gHG(gDKT3-7) combinations have been analyzed in more detail.

Large scale COS cell expression preparations were made and the humanized antibody was affinity purified by Protein A. Relative binding affinities were measured. FIG. 3A and FIG. 3B show results from two such experiments. The affinity of mOKT3 for antigen ($K_a$) was measured to be $1.2 \times 10^9$ $M^{-1}$ by Scatchard analysis. This value for mOKT3 compares well to that of $1.3 \times 10^9$ $M^{-1}$ determined previously (Gergely, 1990). In FIG. 3A, gOKT3-5 was compared with cOKT3 and mOKT3 for competition against mOKT3. Values of $1.2 \times 10^9$ $M^{-1}$ and $1.1 \times 10^9$ $M^{-1}$ were obtained for the cOKT3 and gOKT3-5 antibodies respectively.

Figure 4:
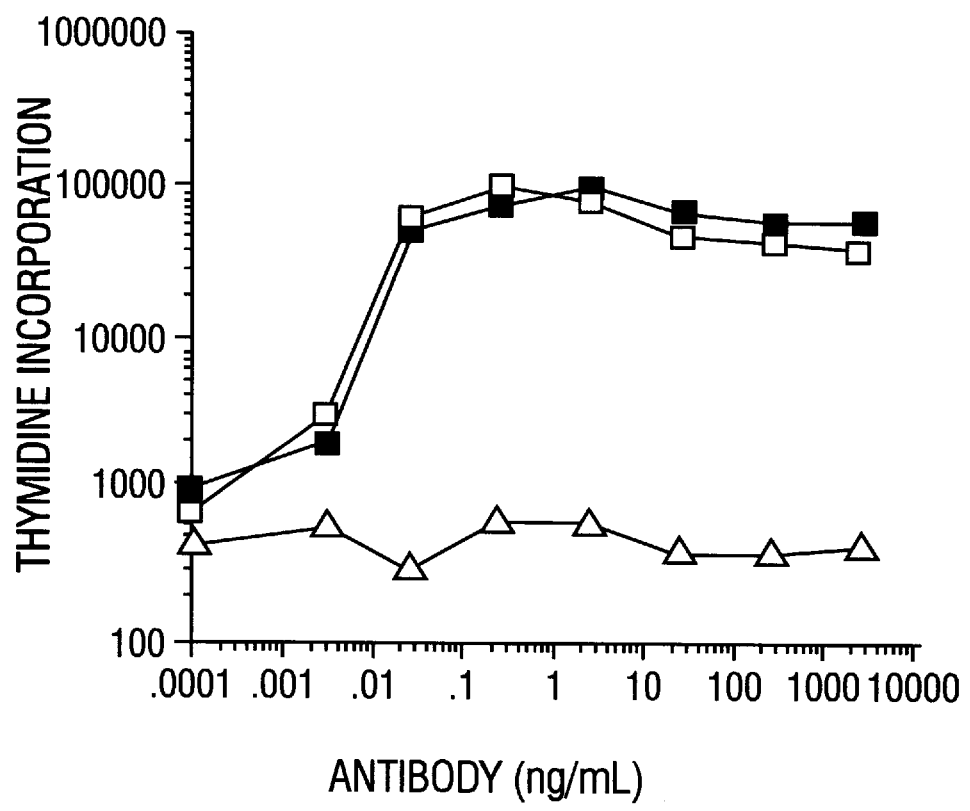
FIG. 4. Proliferation Assay. Proliferation of human PBMC to anti-CD3 antibody produced by COS cell transfection. PBMC were incubated for 68 hours in the presence of increasing amounts of anti-CD3 antibody, then pulsed with $^3$H-thymidine for an additional 4 hours, and the incorporation of $^3$H-thymidine quantitated; closed squares: Orthomune® OKT3; open squares: gOKT3-7(γ4); open triangles: mOKT4A FIG. 5. OKT3 displacement assay. Serial dilutions of the "humanized" mAbs were used to competitively inhibit the binding of labeled OKT3 to the CD3 complex, as described in the examples. Values are expressed as a percent of the maximal fluorescence (arbitrary units attributed by the flow cytometer) achieved by binding of the labeled OKT3 alone. The symbols correspond to the following Abs: open circles, gOKT3-6 mAb; closed triangles, gOKT3-5 mAb; open squares, Leu-234 mAb; closed circles, Glu-235 mAb.

Subsequently, (FIG. 3B) similar results were obtained for gOKT3-7 ($K_a$ $1.4 \times 10^9 M^{-1}$) compared to $1.2 \times 10^9$ $M^{-1}$ for mOKT3, $1.4 \times 10^9$ $M^{-1}$ for cOKT3 and $1.1 \times 10^9$ $M^{-1}$ for gOKT3-5. These experiments show that the antigen binding activity of OKT3 has been successfully transferred to the humanized antibodies. Previous studies have indicated that mitogenic potency is a sensitive parameter of the T-cell activation properties of anti-CD3 mabs (Woodle, 1991). In an earlier study it was shown that gOKT3-5 still demonstrated mitogenic potency even in the context of an IgG4 isotype. Therefore, the activation potency of gOKT3-7 antibody was assessed by quantitating proliferating responses. gOKTE-7 demonstrated mitogenic potency equivalent to that of mOKT3 (FIG. 4). This suggests that cross-linking of the bound antibody still occurs with the γ4 isotype leading to proliferative signals. A therapeutic humanized OKT3 antibody may need further alterations to the constant region to minimize such effects.

Example 4

Construction and expression of chimeric OKT3 genes

The murine cDNAs were assembled into expression vector controls for the biological function of the humanized antibodies. The murine variable region cDNA sequences were attached to human κ light chain and γ4 heavy chain constant region DNA sequences following a previously described strategy to generate chimeric OKT3 (cOKT3) genes which were then inserted into eukaryotic expression vectors. As the ultimate aim is to design a humanized OKT3 IgG antibody which can efficiently bind to CD3 while retaining useful effector pharmacokinetics and have no first dose side effects, a reduced affinity for FcR was built into the constructs by using the γ4 gene.

Small scale COS cell expression and metabolic labelling studies were as described (Whittle, 1987). Large scale COS cell expression studies were performed in roller bottles, harvesting the product supernatant 5 days after transfection. (T. Livelli, Specialty Media Inc., Lavallette, N.J.). Material from large scale transfections was purified by Protein A Sepharose chromatography. The yield of assembled antibody in COS cell supernatants was measured as described by Woodle (1992).

Murine OKT3, cOKT3, and murine/chimeric hybrid antibodies expressed from COS cells were shown to bind to antigen equivalently to mOKT3 and to block the binding of (i.e.) mOKT3 to CD3 positive cells.

Example 5
Transient expression of murine and human-OKT3 mAbs genes

COS-1 cell expression studies were performed using reagents and procedures from a transient expression kit (Specialty media, Lavallette, N.J.) modified for use in roller bottles (T. Livelli, Specialty Media, personal communication). Product supernatants for purification of the test Abs were harvested 6 days after transfection.

ELISA assays were performed to determine the yield of assembled "humanized" antibody in COS cells supernatants. Ninety-six well plates were coated with F(ab')$_2$ goat anti-human Fc antibody. COS cell supernatants were added and incubated for one hour at room temperature and washed. Horseradish peroxidase-conjugated goat anti-human kappa chain (Caltag) was used with o-phenylenediamine (OPD) for detection. Purified human IgG was used as standard.

Example 6
Mutated "humanized" OKT3 mAbs bind to the CD3 complex of T-cells with the same affinity as murine OKT3

The Fc portion of the gOKT3-5 mAb was mutated according to procedures described above in order to alter its binding to FcR-bearing cells. A leucine was substituted for a phenylalanine in position 234 (Leu-234), or the adjacent leucine (235) was transformed into a glutamic acid (Glu-235). The affinity of the gOKT3-5 mAb for the TCR complex was previously shown to be similar to that of OKT3 (Van Wauwe, et al., 1980). Although changes in the Fc portion of the mAb should not alter Ab binding affinity, it was important to show that point mutations in the CH2 region of the Ab, close to the hinge, did not impair the binding of the Leu-234 and the Glu-235 mAbs to the CD3 antigen.

A displacement assay was performed to examine the ability of the mutated Abs to competitively inhibit the binding of murine OKT3 to human T-cells. Human peripheral blood acute lymphocytic leukemia cells were re-suspended in flow cytofluorimetry (FCM) buffer at $5 \times 10^5$ cells/mL. Dilutions of the anti-CD3 mAbs were added and incubated at 4° C. for 1 hour. Fluorescein isothiocyanate (FITC) was dissolved in N,N-dimethyl formamide (DMF) to give a 10 mg/mL solution. FITC/DMF was added to purified mAb at 1:10 w/w and incubated at 25° C. for four hours, followed by dialysis into PBS containing an anion exchange resin (AG1-X8, 200–400 mesh, chloride form; Bio-Rad). Aggregates were removed prior to use by airfuge centrifugation (Beckman). A fixed saturating amount of OKT3-FITC was added, and the cells were further incubated for 1 hour at 4° C., washed and analyzed by flow cytofluorimetry (FCM).

One or two-color FCM were performed using a FACScan flow cytometer, interfaced to a Hewlett-Packard 310 computer. Data analysis were performed using Consort-30 software. Logarithmically amplified fluorescence data were collected on 10,000 viable cells, as determined by forward and right angle light scatter intensity. One-color fluorescence data were displayed in histogram mode with fluorescence intensity on the x axis and cell number of the y axis. Two-color fluorescence data were displayed as contour plots with green (FITC) fluorescence on the x axis and orange (phycoerythrin) fluorescence on the y axis. All FCM staining procedures were performed at 4° C. in FCM buffer.

Figure 5:
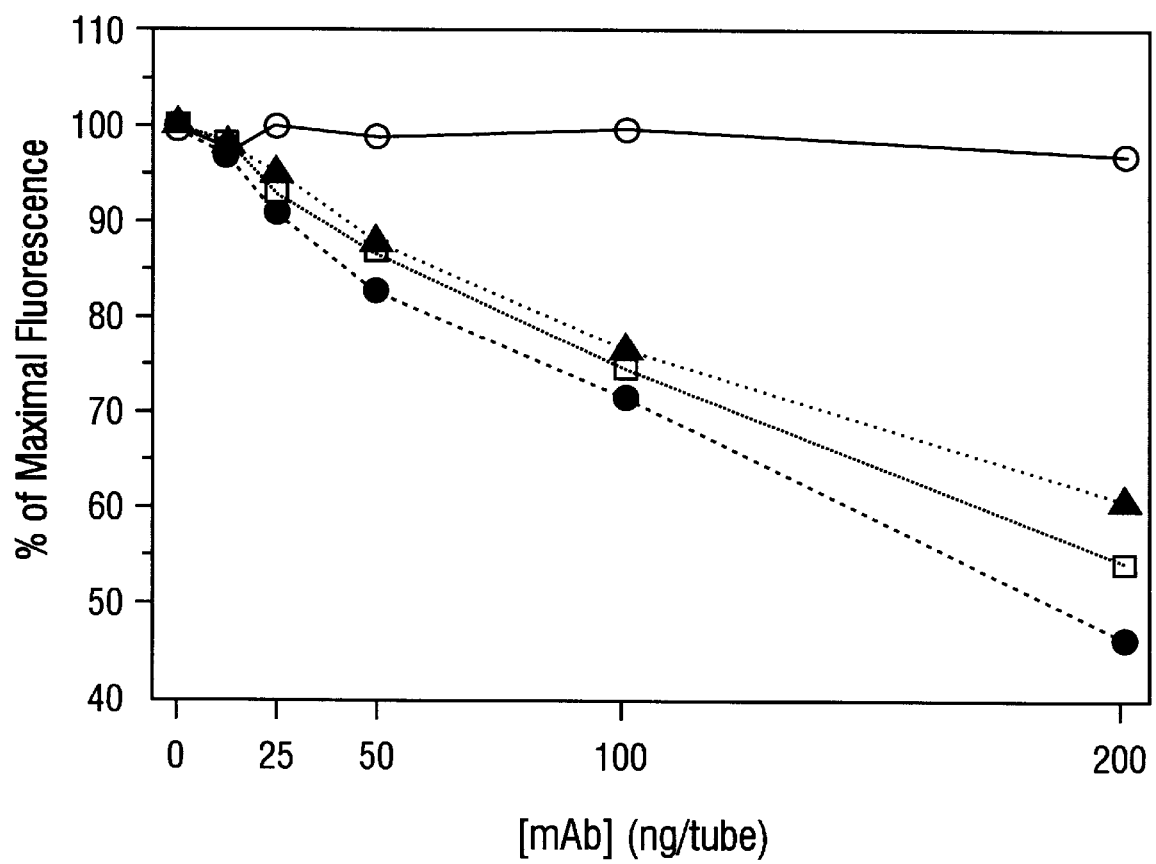

The results of this assay are shown in FIG. 5. The data is presented as % inhibition of maximal fluorescence intensity (determined by OKT3-FITC binding in the absence of blocking Ab). Both mutant Abs displayed a similar affinity for their epitope as the parental gOKT3-5 mAb. In contrast, the gOKT3-6 mAb, a different "humanized" OKT3 which has a very weak binding activity for the CD3 antigen (Van Wauwe, et al., 1980), was unable to displace the OKT3 mAb. These results correlate with the data obtained previously on a panel of isotype-switch variants of murine anti-CD3 mAbs. In those studies, the anti-CD3 mAbs expressing different isotypes had a comparable avidity for the TCR complex as assessed by Scatchard analysis (Van Wauwe, et al., 1980), or by precipitation of the TCR complex and cross-blocking experiments. Thus, any differences in the activation or suppressive properties of the mutated Abs could not be attributed to a modified affinity of the combining site of the anti-CD3 mAbs for T-cells.

Example 7
Binding of the mutant anti-CD3 mAbs to FcR on U937 cells

The mutations generated in the CH2 region of the human IgG4 gOKT3-5 either mimicked the amino acid sequence of the FcR binding region of a human IgG1 (Leu-234), which has a higher affinity for human FcR I than human IgG4, or of a murine IgG2b (Glu-235) that binds weakly to FcR I but still binds to human FcR II. In order to determine the effects of those mutations on FcR binding, the FcR binding affinity of the various "humanized" OKT3 mAbs were tested on the monocytic U937 cell line that bears FcR I and II by displacement of either a PE-coupled murine IgG2a or of a $^{125}$I-labelled human IgG1.

The murine anti-CD5 IgG2a-PE, OKT3E IgG2b, OKT3D IgG2b, OKT3 IgG2a, and a human IgG4 Ab FITC-coupled as described supra, were used to compete for binding in the FcR binding assay. Phycoerythrin-coupled (PE) anti-CD2 and anti-CD5 used as counterstains in the activation assays were purchased from Coulter Immunology. Modulation and coating of the TCR were determined using FITC-coupled OKT3 IgG2a and OKT3D IgG2a as described below.

FcR binding assays were performed using the FcR I- and II-bearing U937 human cell line.

For competitive inhibition assay with PE-coupled murine anti-CD5 IgG2a, $30 \times 10^6$ cells were cultured overnight at 37° C. in complete media in the presence of 500 U/mL of human IFN-γ to enhance the expression of FcR I. The cells were washed three times with DMEM containing 25 μM HEPES, incubated for 2 hours at 37° C. in FCS-free media and washed twice in DMEM and once in flow cytofluorimetry (FCM) buffer (PBS containing 0.1% FCS and 0.1% sodium-azide). Aliquots of the anti-CD3 mAbs serially diluted in FCM buffer were added to 96-well V-bottom tissue culture plates along with 250,000 U937 cells/well. After incubating the cells for 15 mins. at 0° C., 0.3 μg of anti-CD5 was added. Displacement of Fc-mediated anti-CD3 binding was allowed to occur for 90 minutes at 0° C., after which cells were harvested and washed in FCM buffer. Fluorescence of 10,000 cells stained with the PE-anti-CD5 Ab was determined using a FACScan flow cytometer. The data was plotted in a format using Consort 30 software as described below.

For competitive inhibition assay for FcR binding with $^{125}$I-human IgG, U937 cells were washed and re-suspended at a concentration of $1.4 \times 10^8$ cells/mL in the assay medium (0.2% BSA in PBS). Aliquots of $1 \times 10^6$ cells per tube were incubated for 1 hour at 37° C. with $^{125}$I-labeled human IgG at a final concentration of $1 \times 10^{-9}$ M. Murine or "humanized" OKT3 was added at final concentrations ranging from 0.023 μg/ml to 150 μg/mL, with the total volume equating 21 μL/tube. Following the incubation, the mixture was layered over 10% sucrose. Upon centrifugation at 11000 g for 5 mins, the pelleted cells (bound $^{125}$I-huIgG) separated from the medium containing free $^{125}$I-huIgG. The tubes were then frozen in dry ice and the bottom of the tube containing the pelleted cells was removed for analysis of the bound $^{125}$I-huIgG.

The maximum binding of $^{125}$I-huIgG was determined in the absence of the inhibitor. The results are expressed as a percentage of the $^{125}$1-huIgG bound in the presence of the inhibitor relative to the maximum binding. Non-specific binding is seen as the percentage bound in the presence of excess inhibitor (150 μg/ml murine OKT3). All controls and samples were assayed in triplicate tubes.

The N-terminus of the $CH_2$ domain of the mutated constructs is summarized in FIG. 6.

Murine OKT3 IgG2a had, as expected, the highest affinity of all the anti-CD3 mAbs tested for FcR binding to U937 cells. As previously shown for human IgG4 mAbs, the gOKT3-5 required a 10-fold higher concentration to achieve the same inhibition. The Leu-234 mAb, that was expected to enhance FcR I binding, has consistently proven to compete more efficiently for FcR binding than the gOKT3-5 mAb. In contrast, the Glu-235 mAb, bearing the FcR binding region similar to murine IgG2b, bound poorly to U937 cells, requiring a 10-fold higher concentration than the gOKT3-5 and approximately a 100-fold greater concentration than the murine OKT3 to achieve the same percent inhibition. These results indicated that, as anticipated from their respective amino acid sequence in the FcR binding domain, the rank order of binding of the mAbs to U937 cells was murine OKT3>Leu-324>gOKT3-5>Glu-235 mAb.

Example 8
Proliferation Assays

The Glu-235 mAb was tested for its ability to induce T-cell proliferation. Human peripheral blood mononuclear cells (PBMC) were obtained from normal volunteers by Ficoll-hypaque density gradient centrifugation of EDTA-anticoagulated whole blood. EBV-transformed lymphoblastoid cell lines (LCL) and human histiocytoma-derived U937 cell-line were maintained in continuous culture in complete media (DMEM supplemented with 2 mM L-glutamine), 2 mM non-essential amino acids, 100 U/mL penicillin-streptomycin (Gibco), $5 \times 10^5$M 2-mercapto-ethanol (Gibco) and 25 μM HEPES (Gibco) with 10% fetal calf serum (FCS, Gibco).

PBMC preparations were re-suspended in complete DMEM with 1% FCS and aliquotted to 96-well round bottom tissue culture plates (Costar) at $1 \times 10^5$ cells/well. The different Abs were added to the wells by serial log dilutions in culture media. After 72 hours of culture at 37° C. in a 5% $CO_2$ incubator, 1 μCi of $^3$H-thymidine was added to each well and followed by an additional 24 hour incubation. Cells were harvested on a semi-automatic cell harvester and $^3$H-thymidine incorporation was measured in a liquid scintillation counter. All data were expressed as mean CPM of triplicate determinations.

Figure 7:
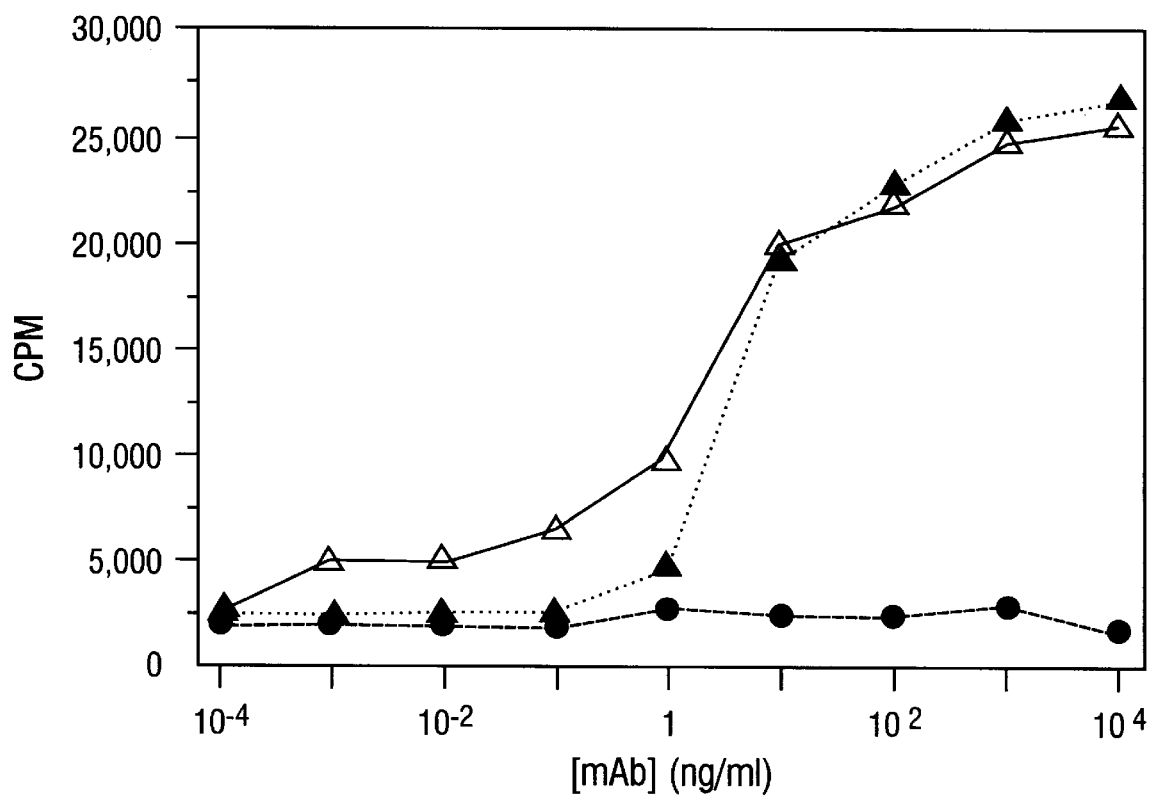
FIG. 7. Mitogenicity induced by murine and "humanized" anti-CD3 mAbs. PBMC were incubated for 72 hours with serial dilutions of the mAbs before the addition of 1 μCi/well of $H^3$ Thymidine. Proliferation is depicted as the mean counts per minute (CPM) of triplicates (SEM<10%). These data are representative of the proliferation obtained with PBMC with 3 different donors. The symbols correspond to the following Abs: open triangles, OKT3; closed triangles, gOKT3-5 mAb; closed circles, Glu-235 mAb.

Stimulation of PBMC with the wild-type gOKT3-5 mAb resulted in cell proliferation comparable to that observed with PBMC stimulated with murine OKT3, as shown in FIG. 7. In contrast, no proliferation was induced by the Glu-235 mAb using PBMC from 3 different donors at mAb concentrations up to 10 μg/mL, suggesting that the alteration of the FcR binding region of this mAb had impaired its mitogenic properties.

Example 9
Activation of T-cells by CDR-grafted mutant mAbs

In order to further analyze early T-cell activation events, human peripheral blood mononuclear cells (PBMC), cultured with various anti-CD3 mAbs, were assessed for cell surface expression of Leu 23 and IL-2 receptor at 12 and 36 hours incubation, respectively.

For studies involving T-cell expression of activation markers, $2 \times 10^6$ PBMC were cultured for either 12 hours (Leu 23 expression) or 36 hours (IL-2 receptor expression) in 24 well tissue culture plates in the presence of varying concentrations of the mAbs.

Figure 8A:
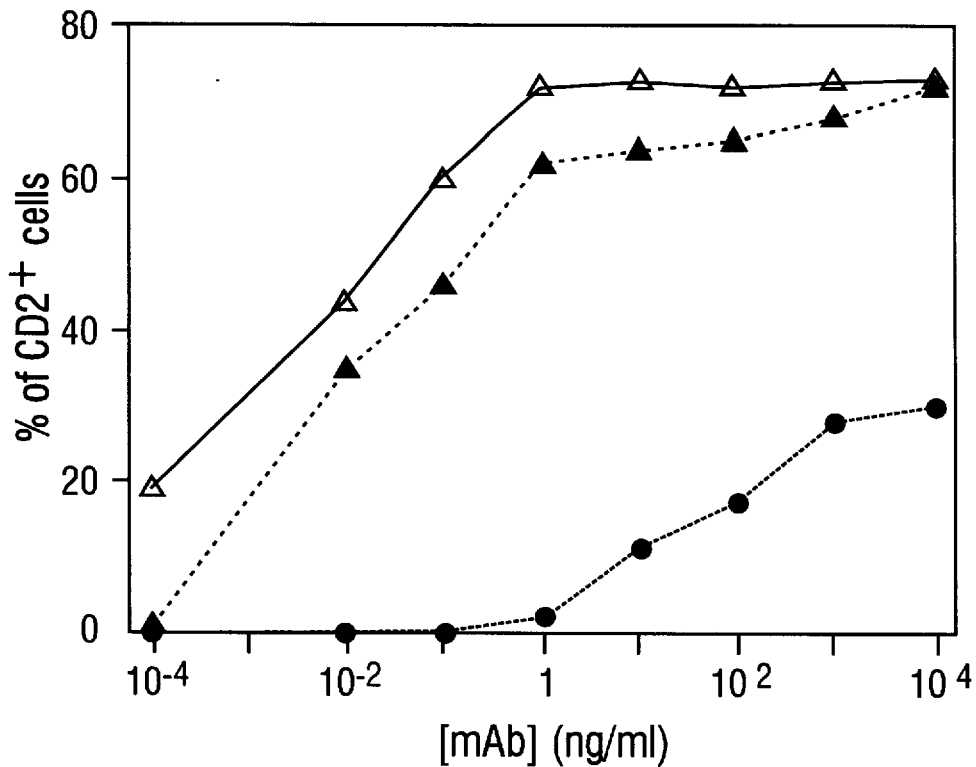
FIG. 8A and FIG. 8B. Expression of markers of activation on the surface of T-cells after stimulation with murine and "humanized" OKT3 mAbs. T-cell expression of Leu 23 (FIG. 8A) and IL-2 (FIG. 3B) receptor was determined after culture of PBMC for 12 or 36 hours respectively, in the presence of varying concentrations of the anti-CD3 mabs. The cells were stained with FITC-coupled anti-Leu 23 or anti-IL-2 receptor Abs and the fraction of T-cells (CD2 or CD5-positive cells, counterstained by PE-coupled Abs) expressing the markers of activation were determined by flow cytofluorimetry (FCM). The symbols correspond to the following Abs: open triangles, OKT3; closed triangles, gOKT3-5 mAb; closed circles, Glu-235 mAb.
Figure 8B:
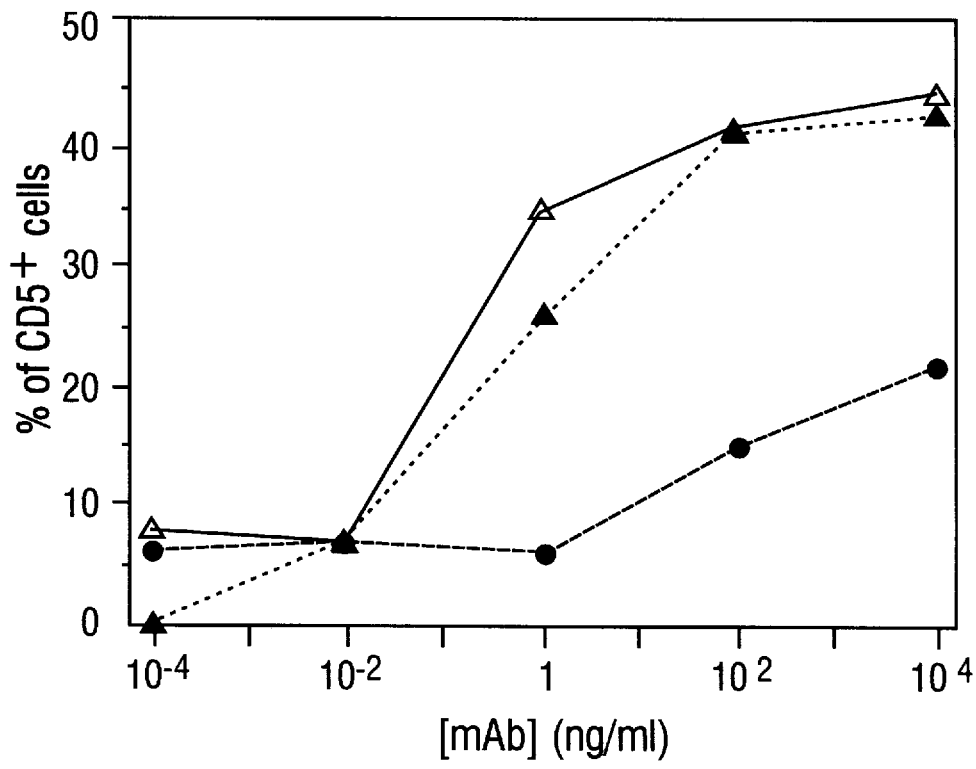

No significant differences were reproducibly observed between murine OKT3 and gOKT3-5 mAb with respect to expression of these cell surface markers (see FIG. 8A and FIG. 8B). In contrast, activation by the Glu-235 mAb resulted in lower levels of expression of both markers. In fact, the highest concentration of the Ab used (10 μg/mL) achieved less than 40% of the maximal activation obtained with standard OKT3. No differences in the expression of these markers were observed between CD4$^+$ and CD8$^+$ cells.

EXAMPLE 10
IFN-γ, GM-CSF and TNF-α production induced by "humanized" OKT3 mAbs

The acute toxicity observed in transplant recipients after the first administration of OKT3 has been attributed to the systematic release of lymphokines triggered by the mAb. Therefore, the in vitro production of GM-CSF, TNF-α and IFN-γ induced by the "humanized" anti-CD3 mAbs was measured. For studies involving lymphokine production, $2 \times 10^6$ PBMC were cultured in 24-well plates for either 24 hours (TNF-α) or 72 hours (GM-CSF and IFN-γ). Tissue culture supernatants were collected at the completion of the respective incubation periods and stored at −20° C. Lymphokine levels were measured via sandwich ELISA techniques using commercially available kits.

Figure 9:
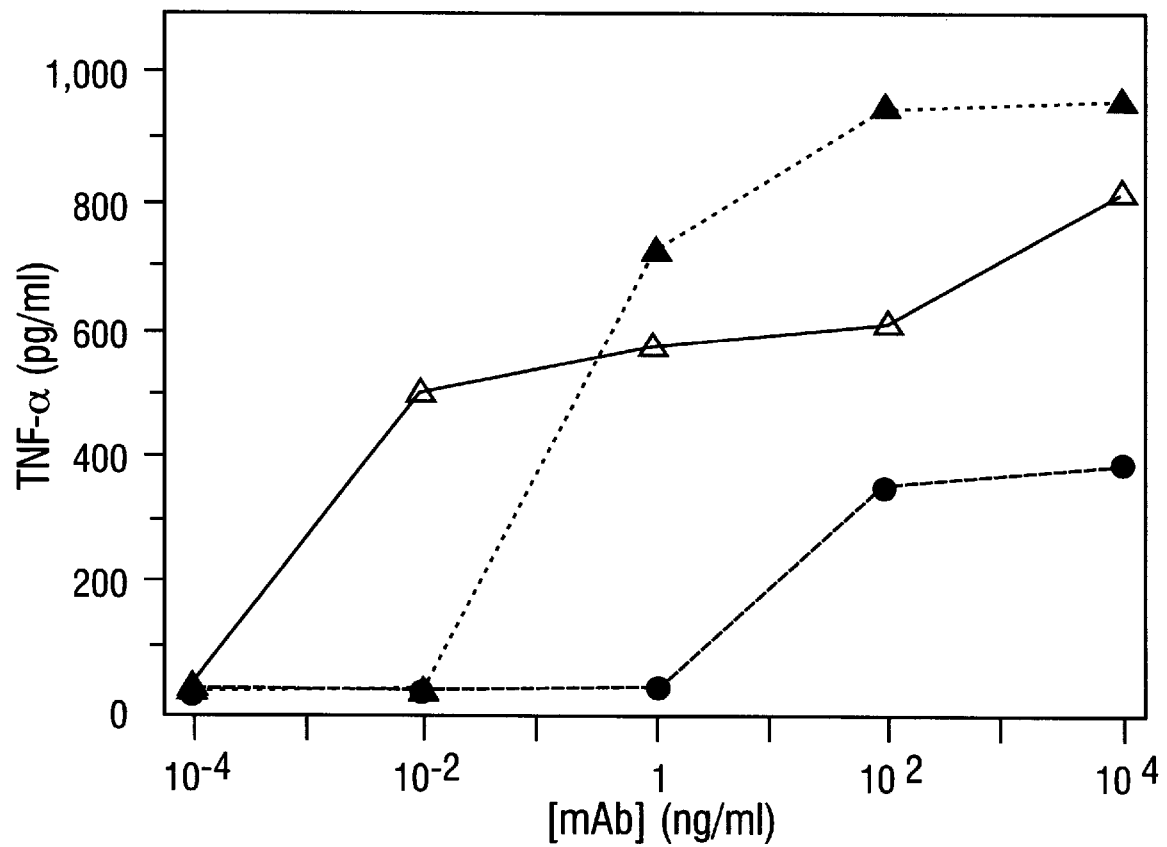
FIG. 9. Release of TNF induced by murine and "humanized" OKT3 mAbs. PBMC were cultured with serial dilutions of the different Abs for 24 hours. The concentration of TNF-α was determined by ELISA, using a commercial kit. Values are expressed as the mean of triplicates (SEM<10%). The symbols correspond to the following Abs: open triangles, OKT3; closed triangles, gOKT3-5 mAb; closed circles, Glu-235 mAb.

Similar amounts of cytokines were produced after culture of PBMC with OKT3 and gOKT3-5 mAb. In contrast, the highest concentration of the Glu-235 mAb induced small quantities of TNF-α (see FIG. 9) and GM-CSF, and no IFN-γ.

Example 11
Induction of modulation and coating of the TCR complex by molecularly engineered OKT3 mAbs The immunosuppressive properties of the different mAbs was compared in vitro. First, the mAbs were examined for their capacity to modulate and/or coat the TCR complex. Human peripheral blood mononuclear cells (PBMC) were incubated at 1×10⁶ cells/mL for 12 hours in 24 well plates with known concentrations of anti-CD3 mAb. PBMC from each group were harvested and stained with either OKT3-FITC or OKT3D-FITC. The fluorescein-stained cells were counterstained with anti-CD5-PE to identify T lymphocytes and analyzed by flow cytofluorimetry (FCM). OKT3D-FITC was selected because of its binding to an epitope distinct from the one binding OKT3 mAb. Thus, this Ab provided a direct measurement of unmodulated surface CD3.

Figure 10A:
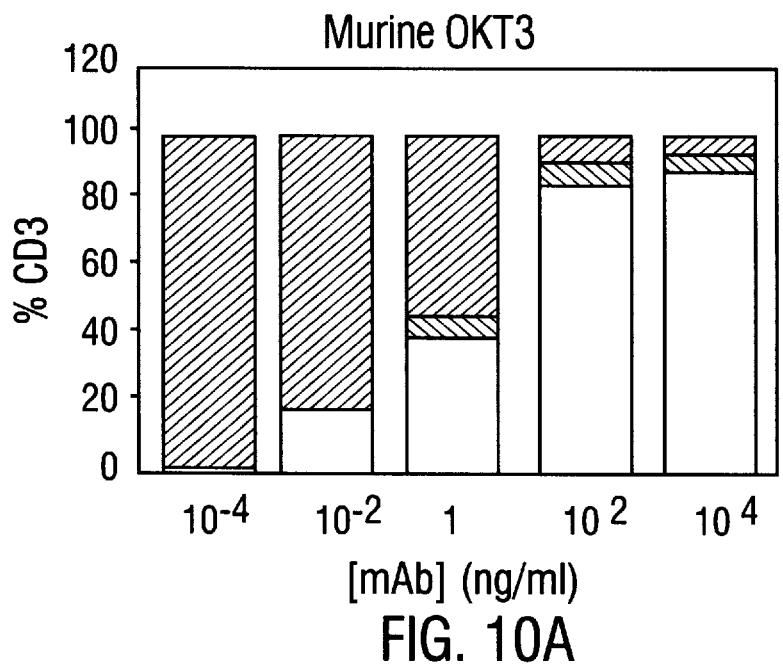
FIG. 10A, FIG. 10B, and FIG. 10C. Modulation and coating of the TCR achieved by the anti-CD3 mAbs. PBMC were incubated for 12 hours with various amounts of the anti-CD3 mAbs. Coating and modulation of the TCR complex was quantitated by FCM as explained in the Examples. T-cells were counterstained with PE-coupled anti-CD5 Ab. The bottom white boxes correspond to the total percentage of CD3 complexes that are modulated, the middle left diagonal cross-hatch boxes to the percentage of CD3 complexes coated by the anti-CD3 mAbs and the upper right diagonal cross-hatch boxes to the percentage of CD3 complexes uncoated on the surface of T lymphocytes.
Figure 10B:
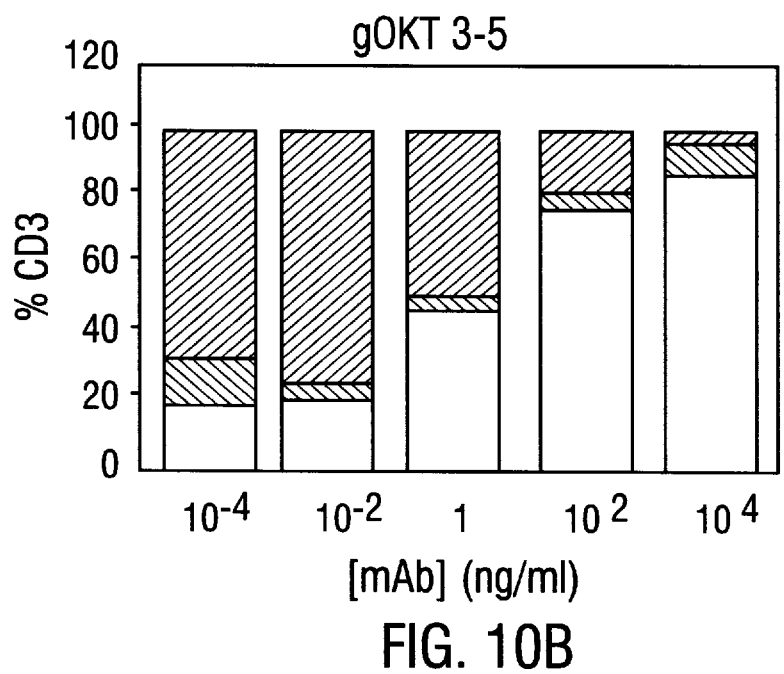
Figure 10C:
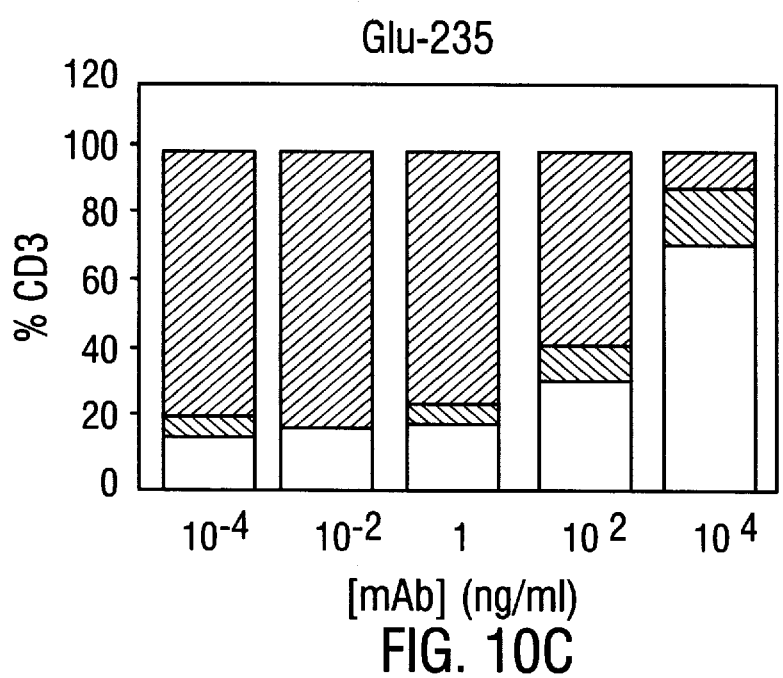

As shown in FIG. 10A, FIG. 10B, and FIG. 10C, the combined modulation and coating of the TCR complex achieved by the gOKT3-5 (FIG. 10B) and murine OKT3 (FIG. 10A) were very similar, with half-maximal TCR blocking achieved at approximately 1 ng/mL. However, the half-maximum modulation plus coating observed with the Glu-235 (FIG. 10C) mAb required 100-fold greater concentrations of mAb (1 $\mu$g/mL) than of murine OKT3. The major difference between the Glu-235 mAb and the other Abs was due to a change in kinetics since, by 48 hours, the mAb coated and modulated the TCR complex similarly to OKT3.

Thus, the achievement by Glu-235 mAb of internalization of the TCR, which may depend on multivalent cross-linking, was delayed as compared with the other anti-CD3 mAbs.

EXAMPLE 12
Inhibition of CTL activity by CDR-grafted mutant mAbs

The ability of the Abs to suppress cytoxicity of alloreactive T-cells was compared. HLA-A2-specific CTL were generated from a normal HLA-A1 donor. Cytolytic activity was assessed on FcR negative-EBV-transformed HLA-A2 target-cells. CTL were generated by a bulk allogeneic MLC technique. Normal human donors were phenotyped for Formulae for calculating CD3 coating and modulation were:

% CD3 Mod. =

$$\frac{\text{Controls Cells } MC_{OKT30-FITC} - Ab\text{-treated cells } MC_{OK3TD-FITC}}{\text{Controls Cells } MC_{OKT3D-FITC}} \times 100$$

$$\% \ CD3 \ \text{Coated} = \frac{Ab\text{-treated Cells } MK_{OKT3D-FITC}}{\text{Controls Cells } MC_{OKT3D-FITC}} -$$

$$\frac{Ab\text{-treated Cells } MC_{OKT3-FITC}}{\text{Controls Cells } MC_{OKT3-FITC}}$$

% CD3 Uncoated + Unmodulated =

100 (% CD3 Coated + % CD3 Modulation)

Where MC represents the mean channel along the x-axis.

HLA-A expression. Responder and stimulator combinations were selected specifically to generate HLA-A2-specific CTL effectors. Responder and stimulator PBMC were prepared by Ficoll-hypaque density gradient centrifugation as described above and re-suspended in RPMI 1640 with 2 mM L-glutamine, 100 U/mL penicillin-streptomycin, 25 $\mu$M HEPES and 15% decomplemented normal human serum. Stimulator PBMC (1×10⁷/mL) were irradiated (3000 rad) and cultured with responder PBMC (1×10⁷/10 mL) in upright 25 cm tissue culture flasks. After 7 days of culture, freshly irradiated stimulator PBMC (4×10⁶/10 mL) were added to 4×10⁶/10 mL of the initial cultured cells and incubated for an additional five days. Cells were then harvested and assayed for CTL activity by $^{51}$Cr release.

HLA-A2-specific CTL effectors were generated as described above, harvested and aliquotted to a 96 well U-bottom tissue culture plate at four different effector/target ratios. Effectors were pre-incubated with serial dilutions of each anti-CD3 mAb for 30 minutes. Following incubation with mAbs, $^{51}$Cr-labeled Fc receptor negative-target-cells [HLA-A2 expressing LCL line (Z2B) or HLA-A1 expressing LCL line (G12B) used as a non-specific target] were added. Spontaneous lysis was measured by incubation of targets alone in media and maximal lysis was achieved by addition of 0.05N HCL. Effectors and targets were co-cultured; supernatant aliquots were harvested and radioactivity was measured in a gamma-counter.

Figure 11:
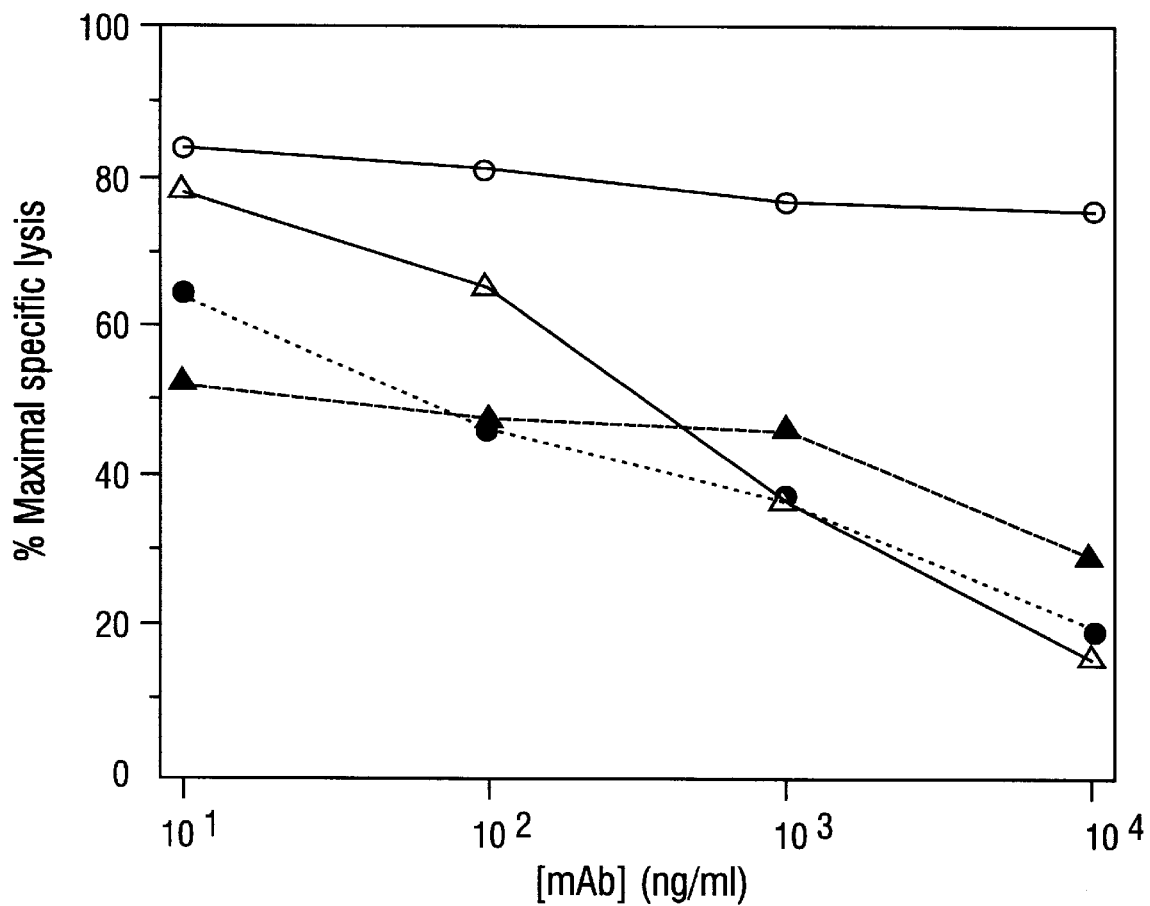
FIG. 11. Inhibition of T-cell cytotoxic activity by "humanized" OKT3 mAbs. HLA A2-specific effector CTLs were generated by secondary mixed lymphocyte culture. Lysis of an A2-expressing LCL target was quantitated by a $^{51}$Cr-release assay. Values are expressed as percent of maximum specific lysis. (Maximum specific lysis was determined to be 60% of the maximum lysis observed with 0.1M HCL). Results represent the mean of triplicates (SEM<10%). The symbols correspond to the following Abs: open circles, gOKT3-6 mAb; open triangles; OKT3; closed triangles, gOKT3-5 mAb; closed circles, Glu-235 mAb.

T-cell cytotoxicity was specific as demonstrated by the absence of lysis of a syngeneic HLA-A1 EBV-transformed cell-line. Inhibition of lysis by anti-CD3 mAbs previously has been attributed to the inability of the T-cells to recognize their targets, due to TCR blockade by the mAb. In the present study, murine OKT3, gOKT3-5 mAb and Glu-235 exhibited a comparable inhibitory effect on the cytolytic activity of the alloreactive T-cells. These results suggest that the ability of the different mAbs to coat the TCR within the 30-min. incubation time was similar (see FIG. 11). In contrast, the gOKT3-6 mAb, a "humanized" OKT3 that has a significantly reduced binding activity for the CD3 antigen, did not inhibit CTL activity. These results suggest that modified affinities for FcRs do not alter the immunosuppressive property of the anti-CD3 mAbs, in vitro.

Example 13
CD4 modulation studies

PBMCs isolated from Ficoll-Hypaque density gradient centrifugation were incubated at 1×10⁶ cell/mL with known concentrations of OKT3 antibodies at 37° C. for 24 hours. The cells were harvested and stained with FITC-OKT4. The cells were counterstained with PE-labelled anti-CD5 (PE-Leu1, Becton Dickinson Immunocytometry Results were calculated using the following formulae:

$$\% \text{ Specific lysis} = \frac{\text{Experimental } CPM - \text{Spontaneous } CPM}{\text{Maximal } CPM - \text{Spontaneous } CPM}$$

$$\% \text{ Maximal specific lysis} = \frac{\% \text{ Specific lysis}_{[mAb]}}{\% \text{ Specific lysis}_{Control}}$$

Where % Specific lysis$_{[mAb]}$ repesents the CPM obtained at a given mAb concentration for a E:T ratio of 25:1 and %

Specific lysis$_{Control}$ represents the CPM obtained in the absence of mAb at the same E:T ratio. Results were expressed as the mean of triplicates.

Systems, San Jose, Calif.) to distinguish T lymphocytes from other PBMCs, and analyzed by FACScan. Data from the resulting studies are reported in FIG. 12A and FIG. 12B.

% CD4 modulation was calculated as follows:

$$\frac{\text{Control } MNC_{FITC-OKT4} - Ab \text{ treated } MCN_{FITC-OKT4}}{\text{Control } MCN_{FITC-OKT4}} \times 100$$

Figure 12A:
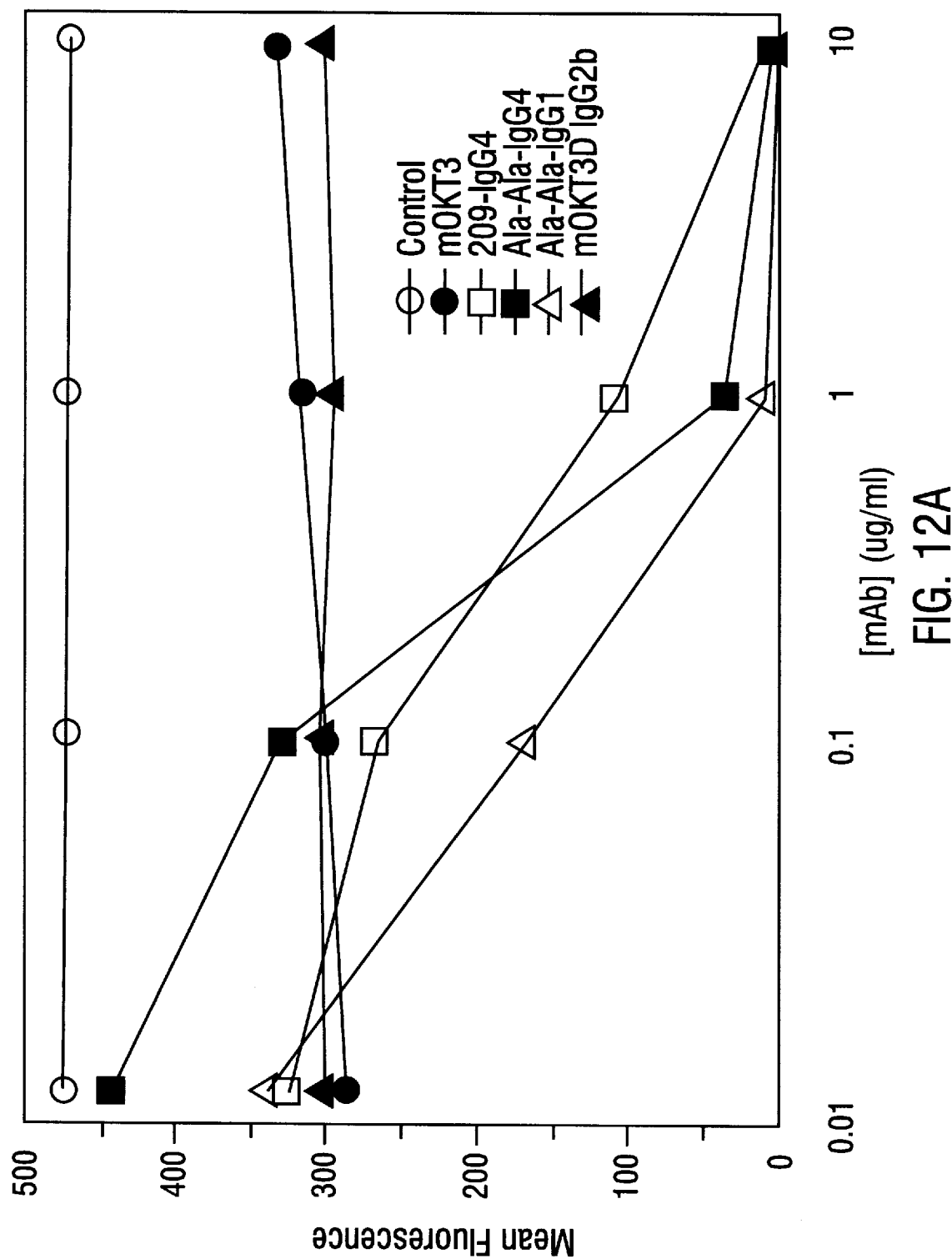
FIG. 12A and FIG. 12B. Variations of mean fluorescence of CD4 (FIG. 12A) and CD8 (FIG. 12B) surface markers induced by anti-CD3 mAbs.

The data in FIG. 12A reveal that the humanized antibodies studied induce the modulation of CD4 in a dose-dependent manner. In contrast is the data for mOKT3 (solid circles), the antibody from which the humanized and mutated antibodies were constructed, had no effect on CD4, as indicated by a straight line plot between antibody concentrations of from 0.01 to 10 $\mu$g/mL. The same can be said for the mOKT3D IgG2b antibody (solid triangles) which has also been neither humanized nor mutated.

Figure 12B:
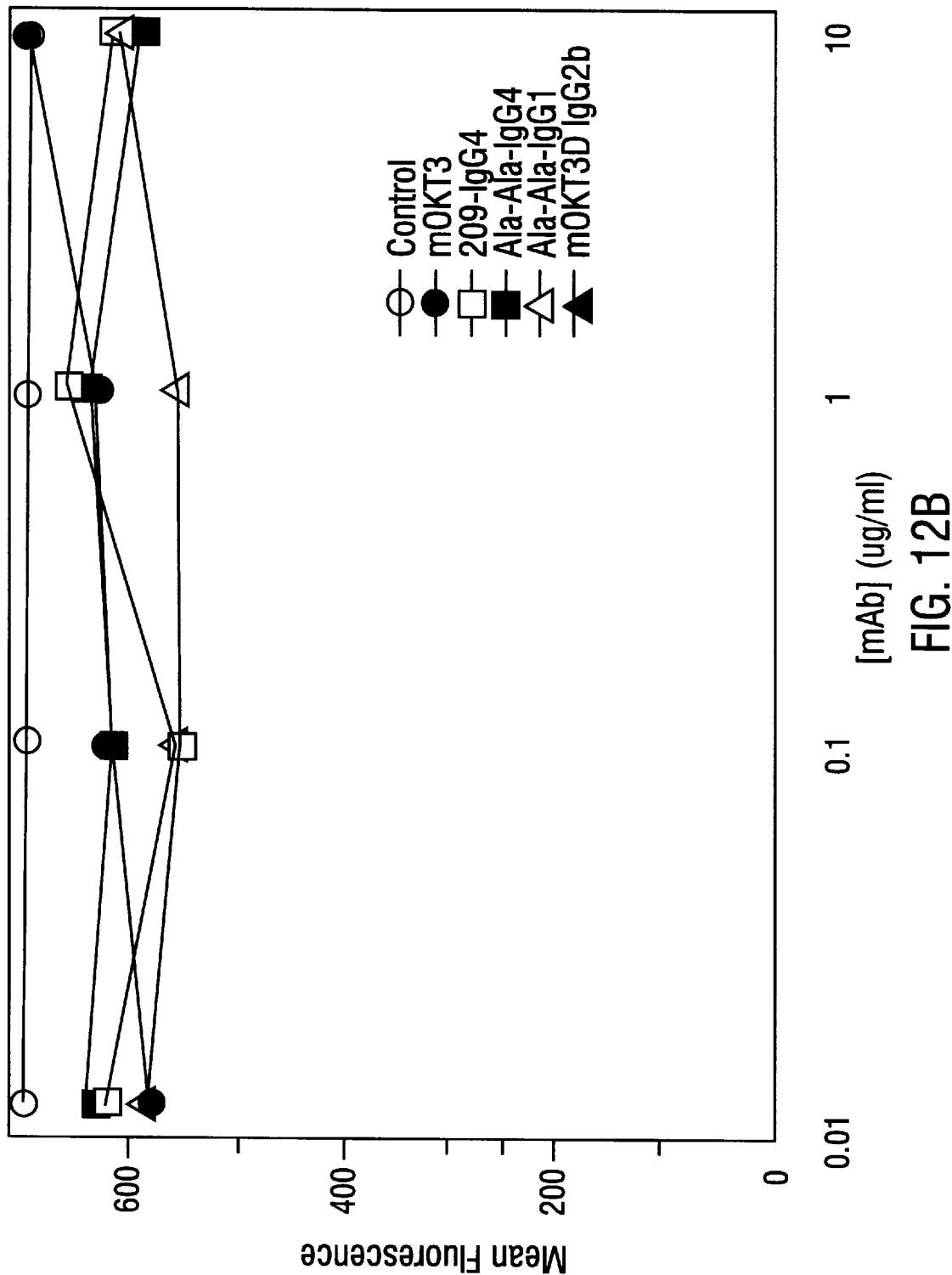

FIG. 12B indicates that, as expected, there is no modulation of CD8 for any of the antibodies studied.

Example 14
ELISA and RES-KW3 studies of CD4 binding

RES-KW3 cells were washed with PBS+0.2% BSA+ 0.1% sodium azide (staining buffer), and first incubated with various concentrations of OKT3 antibodies for 1 hour on ice. The cells were washed three times with cold staining buffer, and FITC-labelled goat anti-human or goat anti-mouse antibodies were added (Caltac Lab. So. San Francisco, Calif.). The cells were incubated on ice for another hour before being washed and subject to FCM.

FCM was performed using a FACScan (Becton-Dickinson Immunocytometry Systems, Mountain View, Calif.) flow cytometer interfaced to a Hewlett-Packard 340 computer, data analyzed using Iysis II software (Becton Dickinson). Fluorescence data were collected using logarithmic amplification on 10,000 viable cells as determined by forward and right angle light scatter intensity. One-color fluorescence data were displayed in histogram mode with fluorescence intensity on the x axis and relative cell number on the y axis.

HIVgp120/CD4 receptor EIA coated microplates from DuPont were used in the CD4 binding assay. 100 $\mu$L/well of CDR-grafted OKT4AIgG1 at various concentrations (1:2 dilution at starting concentration of 50 ng/mL) was added into the wells duplicate for the construction of standard curve. 100 $\mu$L/well of OKT3 antibody samples at various dilutions were then added. The diluent is PBS+10% calf serum+0.05% Tween-20. The plates were incubated at room temperature for 2 hours.

The plates were washed with PBS+0.05% Tween-20 six times before 100 $\mu$L/well of 1:15000 diluted HRPO-conjugated goat anti-human x(f+B) antibodies in diluent was added. The plates were incubated at room temperature for another 2 hours. The plates were washed six times again, and 100 $\mu$L/well of the OPD/hydrogen peroxide solution (five 2-mg OPD tablets were added in 13 mL of Mili-Q water; after they were dissolved, 5 $\mu$L of 30% hydrogen peroxide were then added) was added into each well. The plates were incubated at room temperature in the dark for 30 minutes, and 50 $\mu$L/well of 2.5N HCl was added to stop the reaction. The plates were then read at 490 nm.

Figure 13:
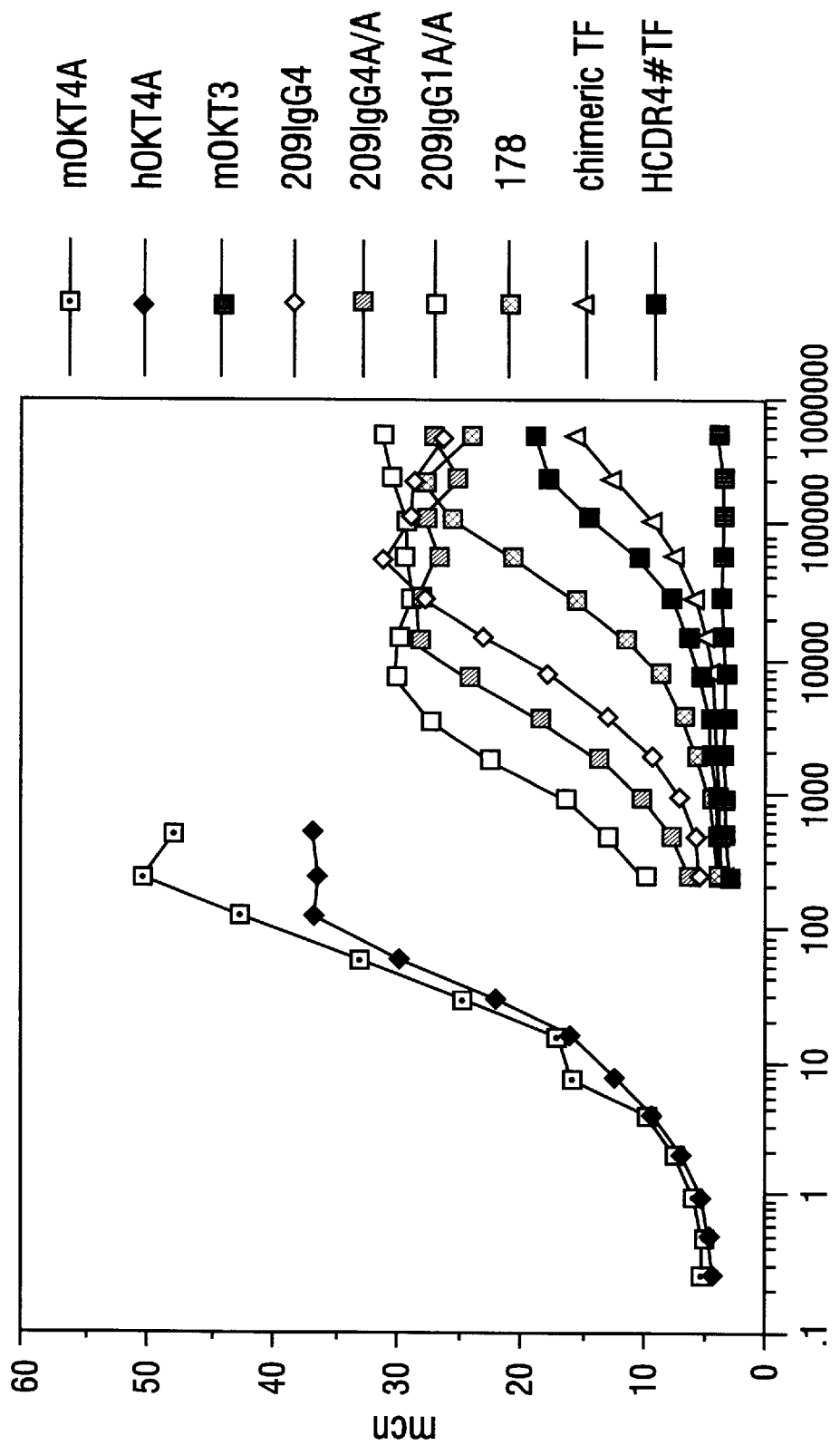
FIG. 13. CD4 binding to RES-KW3 cells.
Figure 14:
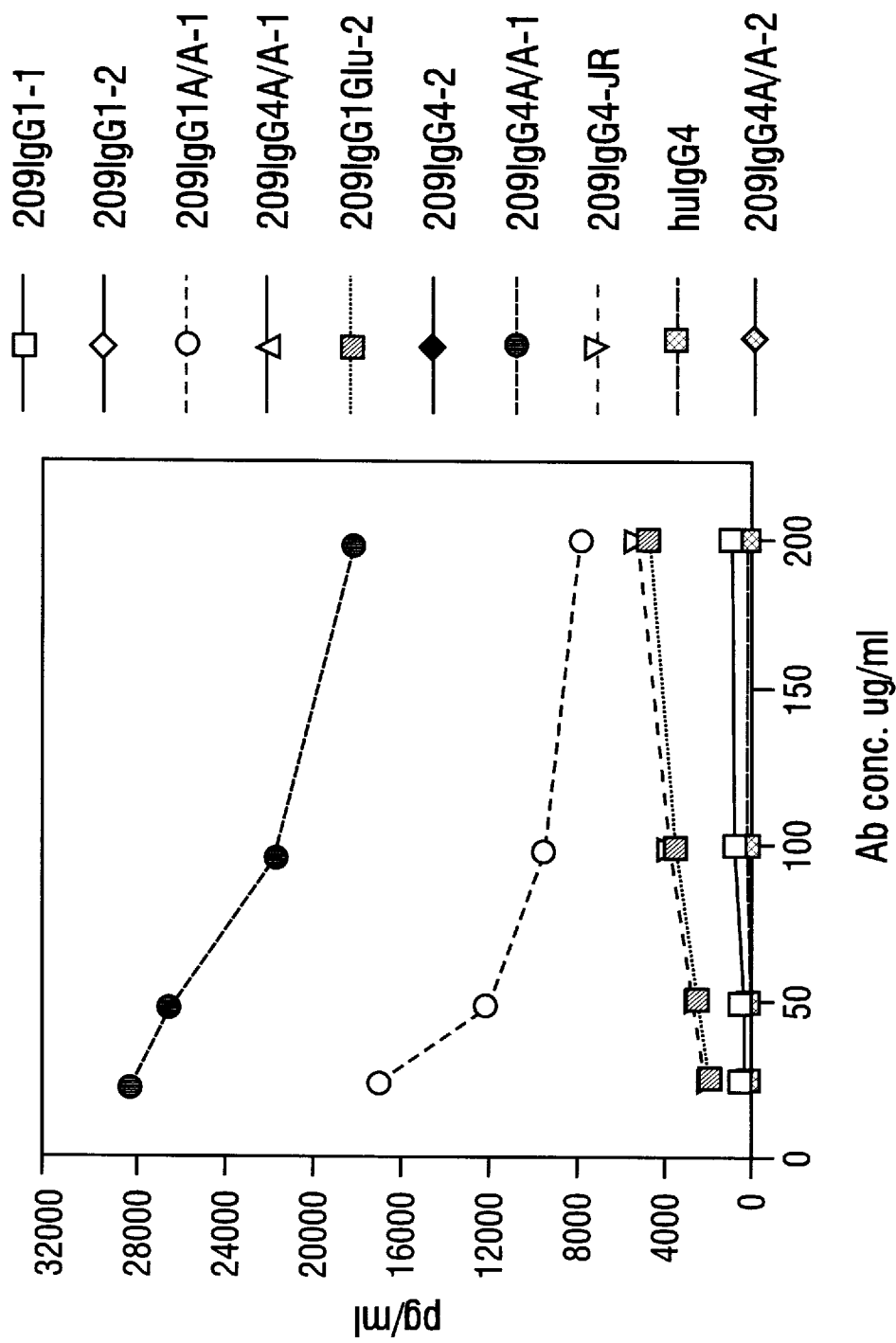
FIG. 14. CD4 binding on ELISA plates.

The resulting data are reported in FIGS. 13 and 14. These data indicate that the humanized OKT3 binds to CD4, either immobilized to ELISA plates or bound to the surface of RES-KW3 cells. It will be appreciated by one skilled in the art that data such as that indicated in FIG. 14 for 209IgG1A/A-1 (open circles) are unexpected, and suggest that divalent binding (binding to both CD3 and CD4, for example), is needed for stable attachment of this antibody to the plate.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter can be made without undue experimentation.

REFERENCES

The following references, to the extent that they provide exemplary procedural or other details supplementary to those set forth herein, are specifically incorporated herein by reference.

Abramowicz D. et al. (1989) *Transplantation.* 47:606.
Adair J. R. (1992) *Immunological Reviews* 130:1.
Alegre M. et al. (1990) *Eur. J. Immunol.* 20:707.
Alegre M.-L. et al. (1992) *J. Immunol.* 148:3461.
Alegre M. et al. (1990) *Transplant. Proc.* 22:1920.
Anderson C. L., R. J. Looney (1986) *Today.* 7:264.
Bentin J. et al. (1991) *Cell. Immunol.* 132:339.
Berzofsky J. A., Berekower I. J. (1984) *Fundamental Immunology*, Paul W. E., ed., 595.
Boot J. H. et al. (1989) *J. Immunol.* 142:1217.
Burton D. R. (1985) *Mol. Immunol.* 22:161.
Chatenoud L. (1989) *Curr. Opin. in Immunol.* 2:246.
Chatenoud L. et al. (1989) *N. Engl. J. Med.* 320:1420.
Chattenoud L. et al. (1990) *Transplantation* 49:697.
Chothia C. et al. (1989) *Nature* 342:877.
Chothia C., Lesk A. M. (1987) *J. Mol. Biol.* 196:901.
Debets J. M. et al. (1989) *J. Immunol.* 144:1304.
Duncan A. R. et al. (1988) *Nature.* 332:563.
Ellenhorn J. D. I. et al. (1992) *Transplantation* In press
Ferran C. et al. (1990) *Eur. J. Immunol.* 20:509.
Frenken L. A. et al. (1991) *Transplantation.* 51:881.
Gergely J. and G. Sarmay (1990) *FASEB J.* 4:3275.
Grantham R., Perrin P. (1986) *Immunology Today* 7:160.
Hale G. et al. (1988) *Lancet ii:*1394.
Hird V. et al. (1991) *Br. J. Cancer* 64:911.
Hirsch R. et al. (1990) *Transplantation.* 49:1117.
Hirsch R. et al. (1991) *J. Immunol.* 147:2088.
Ho S. N. et al. (1989) *Gene* 77:51.
Isaacs J. D. et al. (1992) *Lancet* 340:748.
Jefferies R. et al. (1990) *Mol. Immunol.* 27:1237.
Kabat E. A. et al. (1987) *Washington DC: United States Department of Health and Human Services* 4th Edition.
Klein, J. (1989) *Immunology: The Science of Self-Nonself Discrimination*, Wiley & Sons, N.Y.
Kozak M. (1987) *J. Mol. Biol.* 196:947.
Kramer W. et al. (1984) *Nucl. Acids Res.* 9441.
Krutmann J. et al. (1990) *J. Immunol.* 145:1337.
Laing T. J. and A. Weiss (1988) *J. Immunol.* 140:1056.
Landegren U. et al. (1982) *J. Exp. Med.* 155:1579.
Lanert P. et al. (1991) *Intern. Rev. Immunol.* 17:529.
Ledbetter J. A. et al. (1990) *Sem. Immunol.* 2:99.
Li Y. W. et al. (1990) *Mol. Immunol.* 27:303.
LoBuglio A. F. et al. (1989) *Proc. Natl. Acad. Sci. USA.* 86:4220.
Looney R. J. et al. (1986) *J. Immunol.,* 136:1641.
Lund J. et al. (1991) *J. Immunol.* 147:2657.
Lynch R. G. et al. (1990) *Mol. Immunol.* 27:1167.
Mathieson P. W. et al. (1990) *New Engl. J. Med.* 323:250.
Morikawa S. et al. (1988) *Int. J. Cancer.* 21:166.
Morrison S. L. et al. (1984) *Proc. Natl. Acad. Sci. USA* 81:6351.
Newell K. M. et al. (1990) *Nature* 347:286.
Ollo R. and F. Rougeon (1983) *Cell.* 32:515.
Ortho Multi Center Transplant Study Group (1985) *N. Engl. J. Med.* 313:337.
Parleviet K. J. et al. (1990) *Transplantation.* 50:889.
Partridge L. J. et al. (1986) *Mol. Immunol.* 23:1365.
Perussia B. et al (1983) *J. Exp. Med.* 158:1092.
Petroni K. C. et al. (1988) *J. Immunol.* 140:3467.
Poljak R. (1991) *Mol. Immunol.* 28:1341.
Rao P. E. et al. (1992) *Human Immunol. In press.*
Riechmann L. et al. (1988) *Nature* 332:323.
Routledge E. G. et al. (1991) *Eur. J. Immunol.* 21:2717.
Sahagan B. G. et al. (1986) *J. Immunol.* 137:1066.
Sambrook J. et al. (1989) *Cold Spring Harbor Laboratory Press* 2nd Edition.
Shearman C. W. et al. (1991) *J. Immunol.* 146:928.

Shen L. et al. (1987) *J. Immunol.* 139:534.
Sikder S. K. et al. (1985) *J. Immunol.* 135:4215.
Slameron A. et al. (1991) *J. Immunol.* 147:3047.
Steplewski Z. et al. (1988) *Proc. Natl. Acad. Sci. USA.* 85:4852.
Thistlewaite J. R. et al. (1988) *Am. J. Kidney Dis.* 11:112.
Thistlewaite J. R. Jr. et al. (1984) *Transplantation* 38:695.
Tramontano A. et al. (1990) *J. Mol. Biol.* 215:175.
Transy C. et al. (1989) *Eur. J. Immunol.* 19:947.
van Lier R. A. et al. (1987) *Eur. J. Immunol.* 17:1599.
van Seventer G. A. et al. (1987) *J. Immunol.* 139:2545.
van Lier R. A. et al. (1987) *J. Immunol.* 139:2873.
van Lier R. A. et al. (1989) *Immunology.* 68:45.
Van Wauve J. P. et al. (1984) *J. Immunol.* 133:129.
Van Wauwe J. P. et al. (1980) *J. Immunol.* 124:2708.
Wawrzynczak E. J. et al. (1992) *Mol. Immunol.* 29:221.
Weiss A. et al. (1986) *Ann. Rev. Immunol.* 4:593.
Whittle N. et al. (1987) *Prot. Eng.* 1:499.
Woodle E. S. et al. (1991) *Transplantation* 51:271.
Woodle et al. (1991) *Transplantation* 52:354.
Woodle E. S. et al. (1983) *Transplantation.* 52:361.
Woodle E. S. et al. (1992) *J. Immunol.* 143:2756.
Woof J. M. et al. (1984) *G. Mol. Immunol.* 21:523.
Woof J. M. et al. (1986) *G. Mol. Immunolo.* 23:319.

What is claimed is:

1. A monoclonal antibody comprising a heavy chain having a variable region with a sequence as shown in SEQ ID NO:13 or SEQ ID NO:14 and a human IgG4 constant region, and a light chain having a variable region with a sequence as shown in SEQ ID NO:9 or SEQ ID NO:18, wherein the human IgG4 constant region comprises a point mutation from leucine to glutamic acid at residue 235.

2. A pharmaceutical composition comprising:

a monoclonal antibody comprising a heavy chain having a variable region with a sequence as shown in SEQ ID NO:13 or SEQ ID NO:14 and a human IgG4 constant region, and a light chain having a variable region with a sequence as shown in SEQ ID NO:9 or SEQ ID NO:18, wherein the human IgG4 constant region comprises a point mutation from leucine to glutamic acid at residue 235; and a physiologically acceptable carrier.

3. A method of suppressing rejection of transplanted organ tissue comprising the step of administering to an organ transplant patient, either before, during, or after transplantation, a pharmaceutical composition that comprises an antibody and a physiologically acceptable carrier wherein the antibody is comprised of a heavy chain having a variable region with a sequence as shown in SEQ ID NO:13 or SEQ ID NO:14 and a human IgG4 constant region, and a light chain having a variable region with a sequence as shown in SEQ ID NO:9 or SEQ ID NO:18, wherein the human IgG4 constant region comprises a point mutation from leucine to glutamic acid at residue 235.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 2399 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 53..760

( i x ) FEATURE:
( A ) NAME/KEY: CDS
( B ) LOCATION: 1151..1186

( i x ) FEATURE:
( A ) NAME/KEY: CDS
( B ) LOCATION: 1308..1634

( i x ) FEATURE:
( A ) NAME/KEY: CDS
( B ) LOCATION: 1732..2055

( x i ) SEQUENCE DESCRIPTION: SEQ ID NO:1:

```
ATCCTGGCAA AGATTGTAAT ACGACTCACT ATAGGGCGAA TTCGCCGCCA CC ATG                    55
                                                            Met
                                                             1

GAA TGG AGC TGG GTC TTT CTC TTC TTC CTG TCA GTA ACT ACA GGT GTC                 103
Glu Trp Ser Trp Val Phe Leu Phe Phe Leu Ser Val Thr Thr Gly Val
         5                   10                  15

CAC TCC CAG GTT CAG CTG GTG CAG TCT GGA GGA GGA GTC GTC CAG CCT                 151
His Ser Gln Val Gln Leu Val Gln Ser Gly Gly Gly Val Val Gln Pro
     20                  25                  30

GGA AGG TCC CTG AGA CTG TCT TGT AAG GCT TCT GGA TAC ACC TTC ACT                 199
Gly Arg Ser Leu Arg Leu Ser Cys Lys Ala Ser Gly Tyr Thr Phe Thr
 35                  40                  45

AGA TAC ACA ATG CAC TGG GTC AGA CAG GCT CCT GGA AAG GGA CTC GAG                 247
Arg Tyr Thr Met His Trp Val Arg Gln Ala Pro Gly Lys Gly Leu Glu
 50                  55                  60                  65

TGG ATT GGA TAC ATT AAT CCT AGC AGA GGT TAT ACT AAC TAC AAT CAG                 295
Trp Ile Gly Tyr Ile Asn Pro Ser Arg Gly Tyr Thr Asn Tyr Asn Gln
                 70                  75                  80

AAG GTG AAG GAC AGA TTC ACA ATT TCT AGA GAC AAT TCT AAG AAT ACA                 343
Lys Val Lys Asp Arg Phe Thr Ile Ser Arg Asp Asn Ser Lys Asn Thr
             85                  90                  95
```

```
GCC TTC CTG CAG ATG GAC TCA CTC AGA CCT GAG GAT ACC GGA GTC TAT        391
Ala Phe Leu Gln Met Asp Ser Leu Arg Pro Glu Asp Thr Gly Val Tyr
100                     105                     110

TTT TGT GCT AGA TAT TAC GAT GAC CAC TAC TGT CTG GAC TAC TGG GGC        439
Phe Cys Ala Arg Tyr Tyr Asp Asp His Tyr Cys Leu Asp Tyr Trp Gly
115                     120                     125

CAA GGT ACC CCG GTC ACC GTG AGC TCA GCT TCC ACC AAG GGC CCA TCC        487
Gln Gly Thr Pro Val Thr Val Ser Ser Ala Ser Thr Lys Gly Pro Ser
130                     135                     140                145

GTC TTC CCC CTG GCG CCC TGC TCC AGG AGC ACC TCC GAG AGC ACA GCC        535
Val Phe Pro Leu Ala Pro Cys Ser Arg Ser Thr Ser Glu Ser Thr Ala
            150                     155                     160

GCC CTG GGC TGC CTG GTC AAG GAC TAC TTC CCC GAA CCG GTG ACG GTG        583
Ala Leu Gly Cys Leu Val Lys Asp Tyr Phe Pro Glu Pro Val Thr Val
            165                     170                     175

TCG TGG AAC TCA GGC GCC CTG ACC AGC GGC GTG CAC ACC TTC CCG GCT        631
Ser Trp Asn Ser Gly Ala Leu Thr Ser Gly Val His Thr Phe Pro Ala
            180                     185                     190

GTC CTA CAG TCC TCA GGA CTC TAC TCC CTC AGC AGC GTG GTG ACC GTG        679
Val Leu Gln Ser Ser Gly Leu Tyr Ser Leu Ser Ser Val Val Thr Val
    195                     200                     205

CCC TCC AGC AGC TTG GGC ACG AAG ACC TAC ACC TGC AAC GTA GAT CAC        727
Pro Ser Ser Ser Leu Gly Thr Lys Thr Tyr Thr Cys Asn Val Asp His
210                     215                     220             225

AAG CCC AGC AAC ACC AAG GTG GAC AAG AGA GTT GGTGAGAGGC CAGCACAGGG      780
Lys Pro Ser Asn Thr Lys Val Asp Lys Arg Val
                    230                 235

AGGGAGGGTG TCTGCTGGAA GCCAGGCTCA GCCTCCTGC CTGGACGCAC CCCGGCTGTG       840

CAGCCCCAGC CCAGGGCAGC AAGGCATGCC CCATCTGTCT CCTCACCCGG AGGCCTCTGA      900

CCACCCCACT CATGCTCAGG GAGAGGGTCT TCTGGATTTT TCCACCAGGC TCCCGGCACC      960

ACAGGCTGGA TGCCCCTACC CCAGGCCCTG CGCATACAGG GCAGGTGCTG CGCTCAGACC     1020

TGCCAAGAGC CATATCCGGG AGGACCCTGC CCCTGACCTA AGCCCACCCC AAAGGCCAAA     1080

CTCTCCACTC CCTCAGCTCA GACACCTTCT CTCCTCCCAG ATCTGAGTAA CTCCCAATCT     1140

TCTCTCTGCA GAG TCC AAA TAT GGT CCC CCA TGC CCA TCA TGC CCA             1186
           Glu Ser Lys Tyr Gly Pro Pro Cys Pro Ser Cys Pro
           1           5                   10

GGTAAGCCAA CCCAGGCCTC GCCCTCCAGC TCAAGGCGGG ACAGGTGCCC TAGAGTAGCC     1246

TGCATCCAGG GACAGGCCCC AGCCGGGTGC TGACGCATCC ACCTCCATCT CTTCCTCAGC     1306

A CCT GAG TTC CTG GGG GGA CCA TCA GTC TTC CTG TTC CCC CCA AAA         1352
  Pro Glu Phe Leu Gly Gly Pro Ser Val Phe Leu Phe Pro Pro Lys
  1           5                   10                      15

CCC AAG GAC ACT CTC ATG ATC TCC CGG ACC CCT GAG GTC ACG TGC GTG       1400
Pro Lys Asp Thr Leu Met Ile Ser Arg Thr Pro Glu Val Thr Cys Val
                20                      25                  30

GTG GTG GAC GTG AGC CAG GAA GAC CCC GAG GTC CAG TTC AAC TGG TAC       1448
Val Val Asp Val Ser Gln Glu Asp Pro Glu Val Gln Phe Asn Trp Tyr
                35                  40                      45

GTG GAT GGC GTG GAG GTG CAT AAT GCC AAG ACA AAG CCG CGG GAG GAG       1496
Val Asp Gly Val Glu Val His Asn Ala Lys Thr Lys Pro Arg Glu Glu
            50                  55                      60

CAG TTC AAC AGC ACG TAC CGT GTG GTC AGC GTC CTC ACC GTC CTG CAC       1544
Gln Phe Asn Ser Thr Tyr Arg Val Val Ser Val Leu Thr Val Leu His
65                      70                      75

CAG GAC TGG CTG AAC GGC AAG GAG TAC AAG TGC AAG GTC TCC AAC AAA       1592
Gln Asp Trp Leu Asn Gly Lys Glu Tyr Lys Cys Lys Val Ser Asn Lys
80                  85                      90                  95
```

```
GGC CTC CCG TCC TCC ATC GAG AAA ACC ATC TCC AAA GCC AAA                              1634
Gly Leu Pro Ser Ser Ile Glu Lys Thr Ile Ser Lys Ala Lys
            100                     105

GGTGGGACCC ACGGGGTGCG AGGGCCACAC GGACAGAGGC CAGCTCGGCC CACCCTCTGC                    1694

CCTGGGAGTG ACCGCTGTGC CAACCTCTGT CCCTACA GGG CAG CCC CGA GAG CCA                     1749
                                          Gly Gln Pro Arg Glu Pro
                                            1               5

CAG GTG TAC ACC CTG CCC CCA TCC CAG GAG GAG ATG ACC AAG AAC CAG                      1797
Gln Val Tyr Thr Leu Pro Pro Ser Gln Glu Glu Met Thr Lys Asn Gln
            10                  15                  20

GTC AGC CTG ACC TGC CTG GTC AAA GGC TTC TAC CCC AGC GAC ATC GCC                      1845
Val Ser Leu Thr Cys Leu Val Lys Gly Phe Tyr Pro Ser Asp Ile Ala
        25                  30                  35

GTG GAG TGG GAG AGC AAT GGG CAG CCG GAG AAC AAC TAC AAG ACC ACG                      1893
Val Glu Trp Glu Ser Asn Gly Gln Pro Glu Asn Asn Tyr Lys Thr Thr
    40                  45                  50

CCT CCC GTG CTG GAC TCC GAC GGC TCC TTC TTC CTC TAC AGC AGG CTA                      1941
Pro Pro Val Leu Asp Ser Asp Gly Ser Phe Phe Leu Tyr Ser Arg Leu
55              60                  65                      70

ACC GTG GAC AAG AGC AGG TGG CAG GAG GGG AAT GTC TTC TCA TGC TCC                      1989
Thr Val Asp Lys Ser Arg Trp Gln Glu Gly Asn Val Phe Ser Cys Ser
                75                  80                  85

GTG ATG CAT GAG GCT CTG CAC AAC CAC TAC ACA CAG AAG AGC CTC TCC                      2037
Val Met His Glu Ala Leu His Asn His Tyr Thr Gln Lys Ser Leu Ser
            90                  95                  100

CTG TCT CTG GGT AAA TGAGTGCCAG GGCCGGCAAG CCCCCGCTCC CCGGGCTCTC                      2092
Leu Ser Leu Gly Lys
            105

GGGGTCGCGC GAGGATGCTT GGCACGTACC CCGTCTACAT ACTTCCCAGG CACCCAGCAT                    2152

GGAAATAAAG CACCCACCAC TGCCCTGGGC CCCTGTGAGA CTGTGATGGT TCTTTCCACG                    2212

GGTCAGGCCG AGTCTGAGGC CTGAGTGACA TGAGGGAGGC AGAGCGGGTC CCACTGTCCC                    2272

CACACTGGCC CAGGCGTTGC AGTGTGTCCT GGGCCACCTA GGGTGGGGCT CAGCCAGGGG                    2332

CTCCCTCGGC AGGGTGGGGC ATTTGCCAGC GTGGCCCTCC CTCCAGCAGC AGGACTCTAG                    2392

AGGATCC                                                                              2399
```

( 2 ) INFORMATION FOR SEQ ID NO:2:

( i ) SEQUENCE CHARACTERISTICS:
        ( A ) LENGTH: 236 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Trp Ser Trp Val Phe Leu Phe Phe Leu Ser Val Thr Thr Gly
 1               5                  10                  15

Val His Ser Gln Val Gln Leu Val Gln Ser Gly Gly Gly Val Val Gln
            20                  25                  30

Pro Gly Arg Ser Leu Arg Leu Ser Cys Lys Ala Ser Gly Tyr Thr Phe
        35                  40                  45

Thr Arg Tyr Thr Met His Trp Val Arg Gln Ala Pro Gly Lys Gly Leu
    50                  55                  60

Glu Trp Ile Gly Tyr Ile Asn Pro Ser Arg Gly Tyr Thr Asn Tyr Asn
65              70                  75                      80

Gln Lys Val Lys Asp Arg Phe Thr Ile Ser Arg Asp Asn Ser Lys Asn
                85                  90                  95
```

-continued

Thr Ala Phe Leu Gln Met Asp Ser Leu Arg Pro Glu Asp Thr Gly Val
            100             105                 110

Tyr Phe Cys Ala Arg Tyr Tyr Asp Asp His Tyr Cys Leu Asp Tyr Trp
        115             120             125

Gly Gln Gly Thr Pro Val Thr Val Ser Ser Ala Ser Thr Lys Gly Pro
    130             135             140

Ser Val Phe Pro Leu Ala Pro Cys Ser Arg Ser Thr Ser Glu Ser Thr
145             150             155                         160

Ala Ala Leu Gly Cys Leu Val Lys Asp Tyr Phe Pro Glu Pro Val Thr
            165             170             175

Val Ser Trp Asn Ser Gly Ala Leu Thr Ser Gly Val His Thr Phe Pro
        180             185             190

Ala Val Leu Gln Ser Ser Gly Leu Tyr Ser Leu Ser Ser Val Val Thr
        195             200             205

Val Pro Ser Ser Ser Leu Gly Thr Lys Thr Tyr Thr Cys Asn Val Asp
        210             215             220

His Lys Pro Ser Asn Thr Lys Val Asp Lys Arg Val
225             230             235

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Glu Ser Lys Tyr Gly Pro Pro Cys Pro Ser Cys Pro
1               5               10

( 2 ) INFORMATION FOR SEQ ID NO:4:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Pro Glu Phe Leu Gly Gly Pro Ser Val Phe Leu Phe Pro Pro Lys Pro
1               5               10              15

Lys Asp Thr Leu Met Ile Ser Arg Thr Pro Glu Val Thr Cys Val Val
            20              25              30

Val Asp Val Ser Gln Glu Asp Pro Glu Val Gln Phe Asn Trp Tyr Val
        35              40              45

Asp Gly Val Glu Val His Asn Ala Lys Thr Lys Pro Arg Glu Glu Gln
    50              55              60

Phe Asn Ser Thr Tyr Arg Val Val Ser Val Leu Thr Val Leu His Gln
65              70              75              80

Asp Trp Leu Asn Gly Lys Glu Tyr Lys Cys Lys Val Ser Asn Lys Gly
            85              90              95

Leu Pro Ser Ser Ile Glu Lys Thr Ile Ser Lys Ala Lys
            100             105

( 2 ) INFORMATION FOR SEQ ID NO:5:

( i ) SEQUENCE CHARACTERISTICS:
        ( A ) LENGTH: 107 amino acids (B) TYPE: amino acid
(D) TOPOLOGY: linear (i i) MOLECULE TYPE: protein (x i) SEQUENCE DESCRIPTION: SEQ ID NO:5:

| Gly | Gln | Pro | Arg | Glu | Pro | Gln | Val | Tyr | Thr | Leu | Pro | Pro | Ser | Gln | Glu |
|---|---|---|---|---|---|---|---|---|---|---|---|---|---|---|---|
| 1 | | | | 5 | | | | | 10 | | | | | 15 | |

| Glu | Met | Thr | Lys | Asn | Gln | Val | Ser | Leu | Thr | Cys | Leu | Val | Lys | Gly | Phe |
|---|---|---|---|---|---|---|---|---|---|---|---|---|---|---|---|
| | | | 20 | | | | | 25 | | | | | 30 | | |

| Tyr | Pro | Ser | Asp | Ile | Ala | Val | Glu | Trp | Glu | Ser | Asn | Gly | Gln | Pro | Glu |
|---|---|---|---|---|---|---|---|---|---|---|---|---|---|---|---|
| | | 35 | | | | | 40 | | | | | 45 | | | |

| Asn | Asn | Tyr | Lys | Thr | Thr | Pro | Pro | Val | Leu | Asp | Ser | Asp | Gly | Ser | Phe |
|---|---|---|---|---|---|---|---|---|---|---|---|---|---|---|---|
| | 50 | | | | | 55 | | | | | 60 | | | | |

| Phe | Leu | Tyr | Ser | Arg | Leu | Thr | Val | Asp | Lys | Ser | Arg | Trp | Gln | Glu | Gly |
|---|---|---|---|---|---|---|---|---|---|---|---|---|---|---|---|
| 65 | | | | | 70 | | | | | 75 | | | | | 80 |

| Asn | Val | Phe | Ser | Cys | Ser | Val | Met | His | Glu | Ala | Leu | His | Asn | His | Tyr |
|---|---|---|---|---|---|---|---|---|---|---|---|---|---|---|---|
| | | | | 85 | | | | | 90 | | | | | 95 | |

| Thr | Gln | Lys | Ser | Leu | Ser | Leu | Ser | Leu | Gly | Lys |
|---|---|---|---|---|---|---|---|---|---|---|
| | | | 100 | | | | | 105 | | |

(2) INFORMATION FOR SEQ ID NO:6:

(i) SEQUENCE CHARACTERISTICS:
(A) LENGTH: 107 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:6:

| Gln | Ile | Val | Leu | Thr | Gln | Ser | Pro | Ala | Ile | Met | Ser | Ala | Ser | Pro | Gly |
|---|---|---|---|---|---|---|---|---|---|---|---|---|---|---|---|
| 1 | | | | 5 | | | | | 10 | | | | | 15 | |

| Glu | Lys | Val | Thr | Met | Thr | Cys | Ser | Ala | Ser | Ser | Ser | Val | Ser | Tyr | Met |
|---|---|---|---|---|---|---|---|---|---|---|---|---|---|---|---|
| | | | 20 | | | | | 25 | | | | | 30 | | |

| Asn | Trp | Tyr | Gln | Gln | Lys | Ser | Gly | Thr | Ser | Pro | Lys | Arg | Trp | Ile | Tyr |
|---|---|---|---|---|---|---|---|---|---|---|---|---|---|---|---|
| | | | 35 | | | | | 40 | | | | | 45 | | |

| Asp | Thr | Ser | Lys | Leu | Ala | Ser | Gly | Val | Pro | Ala | His | Phe | Arg | Gly | Ser |
|---|---|---|---|---|---|---|---|---|---|---|---|---|---|---|---|
| | | 50 | | | | | 55 | | | | | 60 | | | |

| Gly | Ser | Gly | Thr | Ser | Tyr | Ser | Leu | Thr | Ile | Ser | Gly | Met | Glu | Ala | Glu |
|---|---|---|---|---|---|---|---|---|---|---|---|---|---|---|---|
| 65 | | | | | 70 | | | | | 75 | | | | | 80 |

| Asp | Ala | Ala | Thr | Tyr | Tyr | Cys | Gln | Gln | Trp | Ser | Ser | Asn | Pro | Phe | Thr |
|---|---|---|---|---|---|---|---|---|---|---|---|---|---|---|---|
| | | | | 85 | | | | | 90 | | | | | 95 | |

| Phe | Gly | Ser | Gly | Thr | Lys | Leu | Glu | Ile | Asn | Arg |
|---|---|---|---|---|---|---|---|---|---|---|
| | | | | 100 | | | | | 105 | |

(2) INFORMATION FOR SEQ ID NO:7:

(i) SEQUENCE CHARACTERISTICS:
(A) LENGTH: 108 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:7:

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Gln | Ala | Ser | Gln | Asp | Ile | Ile | Lys | Tyr |
|---|---|---|---|---|---|---|---|---|---|---|---|---|---|---|---|
| | | | 20 | | | | | 25 | | | | | 30 | | |

```
Leu Asn Trp Tyr Gln Gln Thr Pro Gly Lys Ala Pro Lys Leu Leu Ile
         35                  40                  45

Tyr Glu Ala Ser Asn Leu Gln Ala Gly Val Pro Ser Arg Phe Ser Gly
     50                  55                  60

Ser Gly Ser Gly Thr Asp Tyr Thr Phe Thr Ile Ser Ser Leu Gln Pro
 65              70                  75                      80

Glu Asp Ile Ala Thr Tyr Tyr Cys Gln Gln Tyr Gln Ser Leu Pro Tyr
             85                  90                      95

Thr Phe Gly Gln Gly Thr Lys Leu Gln Ile Thr Arg
             100                 105
```

( 2 ) INFORMATION FOR SEQ ID NO:8:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Asp Ile Gln Met Thr Gln Ser Pro Ser Ser Leu Ser Ala Ser Val Gly
 1               5                  10                      15

Asp Arg Val Thr Ile Thr Cys Ser Ala Ser Ser Ser Val Ser Tyr Met
             20                  25                  30

Asn Trp Tyr Gln Gln Thr Pro Gly Lys Ala Pro Lys Leu Leu Ile Tyr
         35                  40                  45

Asp Thr Ser Lys Leu Ala Ser Gly Val Pro Ser Arg Phe Ser Gly Ser
     50                  55                  60

Gly Ser Gly Thr Asp Tyr Thr Phe Thr Ile Ser Ser Leu Gln Pro Glu
 65              70                  75                      80

Asp Ile Ala Thr Tyr Tyr Cys Gln Gln Trp Ser Ser Asn Pro Phe Thr
             85                  90                      95

Phe Gly Gln Gly Thr Lys Leu Gln Ile Thr Arg
             100                 105
```

( 2 ) INFORMATION FOR SEQ ID NO:9:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Asp Ile Gln Met Thr Gln Ser Pro Ser Ser Leu Ser Ala Ser Val Gly
 1               5                  10                      15

Asp Arg Val Thr Ile Thr Cys Ser Ala Ser Ser Ser Val Ser Tyr Met
             20                  25                  30

Asn Trp Tyr Gln Gln Thr Pro Gly Lys Ala Pro Lys Arg Trp Ile Tyr
         35                  40                  45

Asp Thr Ser Lys Leu Ala Ser Gly Val Pro Ser Arg Phe Ser Gly Ser
     50                  55                  60

Gly Ser Gly Thr Asp Tyr Thr Phe Thr Ile Ser Ser Leu Gln Pro Glu
 65              70                  75                      80

Asp Ile Ala Thr Tyr Tyr Cys Gln Gln Trp Ser Ser Asn Pro Phe Thr
             85                  90                      95
```

Phe Gly Gln Gly Thr Lys Leu Gln Ile Thr Arg
                    100                     105

(2) INFORMATION FOR SEQ ID NO:10:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Gln Val Gln Leu Gln Gln Ser Gly Ala Glu Leu Ala Arg Pro Gly Ala
    1               5                   10                  15

Ser Val Lys Met Ser Cys Lys Ala Ser Gly Tyr Thr Phe Thr Arg Tyr
                    20                  25                  30

Thr Met His Trp Val Lys Gln Arg Pro Gly Gln Gly Leu Glu Trp Ile
                35                  40                  45

Gly Tyr Ile Asn Pro Ser Arg Gly Tyr Thr Asn Tyr Asn Gln Lys Phe
            50                  55                  60

Lys Asp Lys Ala Thr Leu Thr Thr Asp Lys Ser Ser Ser Thr Ala Tyr
    65                  70                  75                  80

Met Gln Leu Ser Ser Leu Thr Ser Glu Asp Ser Ala Val Tyr Tyr Cys
                    85                  90                  95

Ala Arg Tyr Tyr Asp Asp His Tyr Cys Leu Asp Tyr Trp Gly Gln Gly
                    100                 105                 110

Thr Thr Leu Thr Val Ser Ser
                115

(2) INFORMATION FOR SEQ ID NO:11:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Gln Val Gln Leu Val Glu Ser Gly Gly Val Val Gln Pro Gly Arg
    1               5                   10                  15

Ser Leu Arg Leu Ser Cys Ser Ser Gly Phe Ile Phe Ser Ser Tyr
                    20                  25                  30

Ala Met Tyr Trp Val Arg Gln Ala Pro Gly Lys Gly Leu Glu Trp Val
                35                  40                  45

Ala Ile Ile Trp Asp Asp Gly Ser Asp Gln His Tyr Ala Asp Ser Val
            50                  55                  60

Lys Gly Arg Phe Thr Ile Ser Arg Asp Asn Ser Lys Asn Thr Leu Phe
    65                  70                  75                  80

Leu Gln Met Asp Ser Leu Arg Pro Glu Asp Thr Gly Val Tyr Phe Cys
                    85                  90                  95

Ala Arg Asp Gly Gly His Gly Phe Cys Ser Ser Ala Ser Cys Phe Gly
                    100                 105                 110

Pro Asp Tyr Trp Gly Gln Gly Thr Pro Val Thr Val Ser Ser
                115                 120                 125

(2) INFORMATION FOR SEQ ID NO:12:

( i ) SEQUENCE CHARACTERISTICS:
  ( A ) LENGTH: 119 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:12:

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ser | Ser | Gly | Tyr | Thr | Phe | Thr | Arg | Tyr |
|---|---|---|---|---|---|---|---|---|---|---|---|---|---|---|
| | | | 20 | | | | | 25 | | | | | 30 | |

| Thr | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Tyr | Ile | Asn | Pro | Ser | Arg | Gly | Tyr | Thr | Asn | Tyr | Asn | Gln | Lys | Phe |
|---|---|---|---|---|---|---|---|---|---|---|---|---|---|---|---|
| | | 50 | | | | 55 | | | | | 60 | | | | |

| Lys | Asp | Arg | Phe | Thr | Ile | Ser | Arg | Asp | Asn | Ser | Lys | Asn | Thr | Leu | Phe |
|---|---|---|---|---|---|---|---|---|---|---|---|---|---|---|---|
| 65 | | | | | 70 | | | | | 75 | | | | | 80 |

| Leu | Gln | Met | Asp | Ser | Leu | Arg | Pro | Glu | Asp | Thr | Gly | Val | Tyr | Phe | Cys |
|---|---|---|---|---|---|---|---|---|---|---|---|---|---|---|---|
| | | | | 85 | | | | | 90 | | | | | 95 | |

| Ala | Arg | Tyr | Tyr | Asp | Asp | His | Tyr | Cys | Leu | Asp | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Pro | Val | Thr | Val | Ser | Ser |
|---|---|---|---|---|---|---|
| | | 115 | | | | |

( 2 ) INFORMATION FOR SEQ ID NO:13:

( i ) SEQUENCE CHARACTERISTICS:
  ( A ) LENGTH: 119 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:13:

| Gln | Val | Gln | Leu | Val | Gln | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Lys | Ala | Ser | Gly | Tyr | Thr | Phe | Thr | Arg | Tyr |
|---|---|---|---|---|---|---|---|---|---|---|---|---|---|---|---|
| | | | 20 | | | | | 25 | | | | | 30 | | |

| Thr | Met | His | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Tyr | Ile | Asn | Pro | Ser | Arg | Gly | Tyr | Thr | Asn | Tyr | Asn | Gln | Lys | Phe |
|---|---|---|---|---|---|---|---|---|---|---|---|---|---|---|---|
| | | 50 | | | | 55 | | | | | 60 | | | | |

| Lys | Asp | Arg | Phe | Thr | Ile | Ser | Thr | Asp | Lys | Ser | Lys | Ser | Thr | Ala | Phe |
|---|---|---|---|---|---|---|---|---|---|---|---|---|---|---|---|
| 65 | | | | | 70 | | | | | 75 | | | | | 80 |

| Leu | Gln | Met | Asp | Ser | Leu | Arg | Pro | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Tyr | Tyr | Asp | Asp | His | Tyr | Cys | Leu | Asp | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Pro | Val | Thr | Val | Ser | Ser |
|---|---|---|---|---|---|---|
| | | 115 | | | | |

( 2 ) INFORMATION FOR SEQ ID NO:14:

( i ) SEQUENCE CHARACTERISTICS:
  ( A ) LENGTH: 119 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:14:

| Gln | Val | Gln | Leu | Val | Gln | Ser | Gly | Gly | Val | Val | Gln | Pro | Gly | Arg |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ser | Leu | Arg | Leu | Ser | Cys | Lys | Ala | Ser | Gly | Tyr | Thr | Phe | Thr | Arg | Tyr |
|     |     |     | 20  |     |     |     |     | 25  |     |     |     |     | 30  |     |
| Thr | Met | His | Trp | Val | Arg | Gln | Ala | Pro | Gly | Lys | Gly | Leu | Glu | Trp | Ile |
|     |     | 35  |     |     |     |     | 40  |     |     |     |     | 45  |     |     |
| Gly | Tyr | Ile | Asn | Pro | Ser | Arg | Gly | Tyr | Thr | Asn | Tyr | Asn | Gln | Lys | Phe |
|     |     | 50  |     |     |     | 55  |     |     |     |     | 60  |     |     |     |
| Lys | Asp | Arg | Phe | Thr | Ile | Ser | Thr | Asp | Lys | Ser | Lys | Ser | Thr | Ala | Phe |
| 65  |     |     |     |     | 70  |     |     |     |     | 75  |     |     |     |     | 80  |
| Leu | Gln | Met | Asp | Ser | Leu | Arg | Pro | Glu | Asp | Thr | Ala | Val | Tyr | Tyr | Cys |
|     |     |     |     | 85  |     |     |     |     | 90  |     |     |     |     | 95  |
| Ala | Arg | Tyr | Tyr | Asp | Asp | His | Tyr | Cys | Leu | Asp | Tyr | Trp | Gly | Gln | Gly |
|     |     |     | 100 |     |     |     |     | 105 |     |     |     |     | 110 |     |
| Thr | Pro | Val | Thr | Val | Ser | Ser |
|     |     | 115 |     |     |     |     |

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TCCAGATGTT AACTGCTCAC                                                  20

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CAGGGGCCAG TGGATGGATA GAC                                       23

( 2 ) INFORMATION FOR SEQ ID NO:17:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GCCGCCACC                                                              9

( 2 ) INFORMATION FOR SEQ ID NO:18:

( i ) SEQUENCE CHARACTERISTICS:
        ( A ) LENGTH: 107 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:18:

| Gln | Ile | Val | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Ser | Ala | Ser | Ser | Ser | Val | Ser | Tyr | Met |
|---|---|---|---|---|---|---|---|---|---|---|---|---|---|---|---|
| | | | 20 | | | | | 25 | | | | | 30 | | |

| Asn | Trp | Tyr | Gln | Gln | Thr | Pro | Gly | Lys | Ala | Pro | Lys | Arg | Trp | Ile | Tyr |
|---|---|---|---|---|---|---|---|---|---|---|---|---|---|---|---|
| | | 35 | | | | | 40 | | | | | 45 | | | |

| Asp | Thr | Ser | Lys | Leu | Ala | Ser | Gly | Val | Pro | Ser | Arg | Phe | Ser | Gly | Ser |
|---|---|---|---|---|---|---|---|---|---|---|---|---|---|---|---|
| | 50 | | | | | 55 | | | | | 60 | | | | |

| Gly | Ser | Gly | Thr | Asp | Tyr | Thr | Phe | Thr | Ile | Ser | Ser | Leu | Gln | Pro | Glu |
|---|---|---|---|---|---|---|---|---|---|---|---|---|---|---|---|
| 65 | | | | | 70 | | | | | 75 | | | | | 80 |

| Asp | Ile | Ala | Thr | Tyr | Tyr | Cys | Gln | Gln | Trp | Ser | Ser | Asn | Pro | Phe | Thr |
|---|---|---|---|---|---|---|---|---|---|---|---|---|---|---|---|
| | | | | 85 | | | | | 90 | | | | | 95 | |

| Phe | Gly | Gln | Gly | Thr | Lys | Leu | Gln | Ile | Thr | Arg |
|---|---|---|---|---|---|---|---|---|---|---|
| | | | 100 | | | | | 105 | | |